(12) United States Patent
Julien et al.

(10) Patent No.: US 9,266,963 B2
(45) Date of Patent: Feb. 23, 2016

(54) ANTIBODIES AND THEIR USE IN THE TREATMENT, PREVENTION AND DIAGNOSIS OF A DISEASE ASSOCIATED WITH SOD1 ABNORMALITIES

(71) Applicant: Universite Laval, Quebec (CA)

(72) Inventors: Jean-Pierre Julien, Quebec (CA); Makoto Urushitani, Shiga (JP)

(73) Assignee: UNIVERSITÉ LAVAL, Quebec (CA)

( * ) Notice: Subject to any disclaimer, the term of this patent is extended or adjusted under 35 U.S.C. 154(b) by 0 days.

(21) Appl. No.: 14/288,374

(22) Filed: May 27, 2014

(65) Prior Publication Data

US 2014/0341927 A1     Nov. 20, 2014

Related U.S. Application Data

(62) Division of application No. 12/065,403, filed as application No. PCT/CA2006/001444 on Aug. 31, 2006, now Pat. No. 8,759,029.

(60) Provisional application No. 60/712,400, filed on Aug. 31, 2005.

(51) Int. Cl.
| | |
|---|---|
| *C07K 16/40* | (2006.01) |
| *G01N 33/573* | (2006.01) |
| *A61P 25/28* | (2006.01) |
| *A61K 39/00* | (2006.01) |

(52) U.S. Cl.
CPC .............. *C07K 16/40* (2013.01); *G01N 33/573* (2013.01); *A61K 2039/505* (2013.01); *C07K 2317/76* (2013.01); *G01N 2333/90283* (2013.01); *G01N 2800/28* (2013.01); *G01N 2800/2821* (2013.01); *G01N 2800/2835* (2013.01)

(58) Field of Classification Search
None
See application file for complete search history.

(56) References Cited

U.S. PATENT DOCUMENTS

| | | | |
|---|---|---|---|
| 5,780,489 | A | 7/1998 | Brooks |
| 5,843,641 | A | 12/1998 | Brown et al. |
| 5,849,290 | A | 12/1998 | Brown et al. |
| 6,420,429 | B1 | 7/2002 | Atlas et al. |
| 6,723,893 | B1 | 4/2004 | Brown et al. |
| 7,439,324 | B2 | 10/2008 | Cashman |

FOREIGN PATENT DOCUMENTS

| | | |
|---|---|---|
| CA | 2157041 A1 | 9/1994 |
| EP | 0279705 A2 | 8/1988 |
| WO | WO-9419493 A1 | 9/1994 |
| WO | WO-2005019828 A1 | 3/2005 |

OTHER PUBLICATIONS

Andrus et al., Protein oxidative damage in a transgenic mouse model of familial amyotrophic lateral sclerosis, J. Neurochem. 71: 2041-2048 (1998).
Boillee et al., Onset and Progression in inherited ALS determined by motor neurons and microglia, Science, 312: 1389-1392 (2006).
Borchelt et al., Superoxide dismutase 1 with mutations linked to familial amyotrophic lateral sclerosis possesses significant activity, Proc. Natl. Acad. Sci. USA, 91: 8292-8296 (1994).
Cleveland et al., From Charcot to Lou Gehrig: Deciphering selective motor neuron death in ALS, Nat. Rev. Neurosc., 2: 806-819 (2001).
Fujiwara, Different Immunoreactivity against Monoclonal Antibodies between Wild-type and Mutant copper/Zinc Superoxide Dismutase linked to Amyotrophic Lateral Sclerosis, The Journal of Biological Chemistry, 280(6): 5061-5070 (2005).
Furukawa et al., Disulfide cross-linked protein represent a significant fraction of ALS-associated Cu, Zn-superoxide dismutase aggregates in spinal cords of model mice, PNAS USA, 103(18): 7148-7153 (2006).
Ihara, Y. et al., Oxidative stress and metal content in blood and cerebrospinal fluid of amyotrophic lateral sclerosis patients with and without a Cu, Zn-superoxide dismutase mutation, Neurol. Res., 27(1):105-8 (2005).
International Search Report for PCT/CA2006/001444, 3 pages (Dec. 22, 2006).
Jones, et al., Replacing the complementarily-determining regions in a human antibody with those from a mouse, Nature, 321: 522-525 (1986).
Jonsson, Minute quantities of misfolded mutant superoxide dismutase-1 cause amyotrophic lateral sclerosis, Brain, 127(1): 73-88 (2004).
Joosten et al., Cellular changes in motoneurons in a transgenic mouse model for amyotrophic lateral sclerosis as revealed by monoclonal antibody Py, Dev. Brain Res. 131: 153-159 (2001).
Kabashi, E. et al., Oxidized/misfolded superoxide dismutase-1: the cause of all amyotrophic lateral sclerosis? Ann. Neurol., 62(6):553-9 (2007).
Kerman, A. et al., Amyotrophic lateral sclerosis is a non-amyloid disease in which extensive misfolding of SOD1 is unique to the familial form, Acta Neuropathol., 119(3):335-44 (2010).
Lee, M. et al., Effect of overexpression of wild-type and mutant Cu/Zn-superoxide dismutases on oxidative damage and antioxidant defences: relevance to Down's syndrome and familial amyotrophic lateral sclerosis, J. Neurochem., 76(4):957-65 (2001).

(Continued)

*Primary Examiner* — Daniel E Kolker
*Assistant Examiner* — Stacey N MacFarlane
(74) *Attorney, Agent, or Firm* — McCarter & English, LLP; Danielle L. Herritt; Emily Dertz

(57) ABSTRACT

The present invention concerns an antibody which specifically binds to an abnormal superoxide dismutase 1 (SOD1), and which neutralizes its pathologic effect when administered to an animal such as a human. The antibody of the invention is a monoclonal antibody produced by hybridoma cell lines deposited with the International Depositary Authority of Canada on Aug. 29, 2006 under accession numbers ADI-290806-01, ADI-290806-02 and ADS-290806-03. The present invention also concerns the use of the antibody of the invention in the treatment, prevention and diagnosis of neurodegenerative diseases such as Amyotrophic lateral sclerosis, Parkinson and Alzheimer in an animal such as a human.

13 Claims, 16 Drawing Sheets

(56) References Cited

OTHER PUBLICATIONS

Liu, H.N. et al., Lack of evidence of monomer/misfolded superoxide dismutase-1 in sporadic amyotrophic lateral sclerosis, Ann. Neurol., 66(1):75-80 (2009).

Muyderman, H. et al., The human G93A-superoxide dismutase-1 mutation, mitochondrial glutathione and apoptotic cell death, Neurochem. Res., 34(10):1847-56 (2009).

Office Action from corresponding Canadian Patent Application No. 2,620,351, dated Dec. 7, 2012.

Office Action from corresponding Japanese Patent Application No. JP-2008-528307, dated Mar. 6, 2012 in Japanese with English translation.

Presta, Antibody engineering, Curr. Op. Struct. Biol., 2: 593-596 (1992).

Reaume, Motor neurons in Cu/Zn superoxide dismutase-deficient mice develop normally but exhibit enhanced cell death after axonal njury, Nat. Genet., 13: 43-47 (1996).

Riechmann et al., Reshaping human antibodies for therapy, Nature, 332: 323-327 (1988).

Rosen et al., Mutations in Cu/Zn superoxide dismutase gene are associated with familial amyotrophic lateral sclerosis, Nature, 362: 59-62 (1993).

Rothstein, J,D., Current hypotheses for the underlying biology of amyotrophic lateral sclerosis, Ann. Neurol., 65 Suppl 1:S3-9 (2009).

Subramaniam et al., Mutant SOD1 causes motor neuron disease independent of copper chaperone-mediated copper loading, Nature Neuroscience, 5(4): 301-307 (2002).

Urushitani et al., CHIP promotes proteasomal degradation of Familial ALS-Linked Mutant SOD1 by Ubiquitinating Hsp/Hsc70, J. Neurochem., 90: 231-244 (2004).

Urushitani et al., Chromogranin-mediated secretion of mutant superoxide dismutase proteins linked to amyotropic lateral sclerosis, Nature Neuroscience, 9(1): 108-118 (2006).

Urushitani et al., Therapeutic effects of immunization with mutant superoxide dismutase in mice models of amyotrophic lateral sclerosis, Proceedings of the National Academy of Sciences of the USA, 104(7): 2495-2500 (2007).

Urushitani, Proteasomal inhibition by misfolded mutant superoxide dismutase 1 induces selective motor neuron death in familial amyotrophic lateral sclerosis, Journal of Neurochemistry, 83: 1030-1042 (2002).

Wang et al., Fibrillar inclusions and motor neuron degeneration in transgenic mice expressing superoxide dismutase 1 with a disrupted copper-binding site, Neurobiology of Disease, 10: 128-138 (2002).

Written Opinion for PCT/CA2006/001444, 6 pages (Dec. 22, 2006).

FIGURE 8

MATKAVCVLKGDGPVQGIINFEQKESNGPVKVWGSIKGLTEGLHGFHVHEFGDNTAGCTSAGPHFNPLSRKHGGPKDEER
HVGDLGNVTADKDGVADVSIEDSVISLSGDHCIIGRTLVVHEKADDLGKGGNEESTKTGNAGSRLACGVIGIAQ

FIGURE 9

```
gtttggggcc agagtgggcg aggcgcggag gtctggccta taaagtagtc gcggagacgg
ggtgctggtt tgcgtcgtag tctcctgcag cgtctggggt ttccgttgca gtcctcggaa
ccaggacctc ggcgtggcct agcgagttat ggcgacgaag gccgtgtgcg tgctgaaggg
cgacggccca gtgcagggca tcatcaattt cgagcagaag gaaagtaatg gaccagtgaa
ggtgtgggga agcattaaag gactgactga aggcctgcat ggattccatg ttcatgagtt
tggagataat acagcaggct gtaccagtgc aggtcctcac tttaatcctc tatccagaaa
acacggtggg ccaaaggatg aagagaggca tgttggagac ttgggcaatg tgactgctga
caaagatggt gtggccgatg tgtctattga agattctgtg atctcactct caggagacca
ttgcatcatt ggccgcacac tggtggtcca tgaaaaagca gatgacttgg gcaaaggtgg
aaatgaagaa agtacaaaga caggaaacgc tggaagtcgt ttggcttgtg gtgtaattgg
gatcgcccaa taaacattcc cttggatgta gtctgaggcc ccttaactca tctgttatcc
tgctagctgt agaaatgtat cctgataaac attaaacact gtaatcttaa aagtgtaatt
gtgtgactttt ttcagagttg ctttaaagta cctgtagtga gaaactgatt tatgatcact
tggaagattt gtatagtttt ataaaactca gttaaaatgt ctgtttcaat gacctgtatt
ttgccagact taaatcacag atgggtatta aacttgtcag aatttctttg tcattcaagc
ctgtgaataa aaaccctgta tggcacttat tatgaggcta ttaaaagaat ccaaattcaa
actaaaaaaa aaaaaaaaaa a
```

FIGURE 10

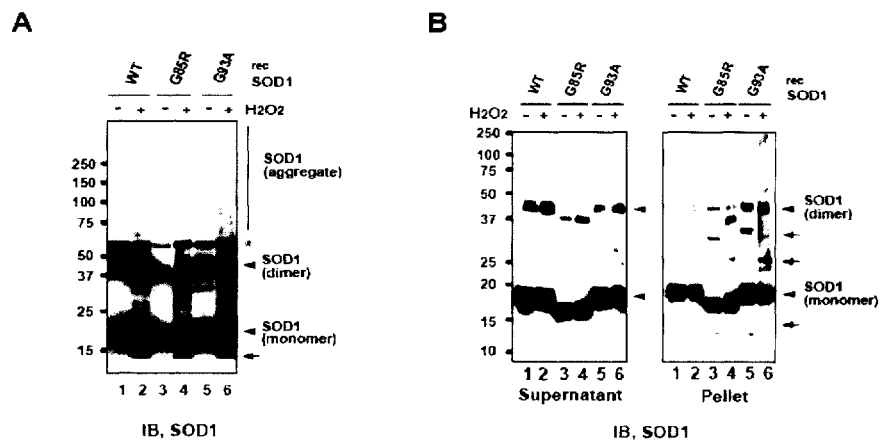

FIGURE 12
A
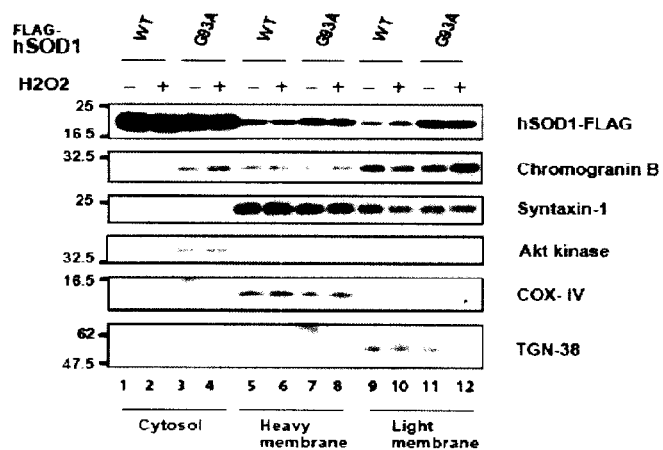
B
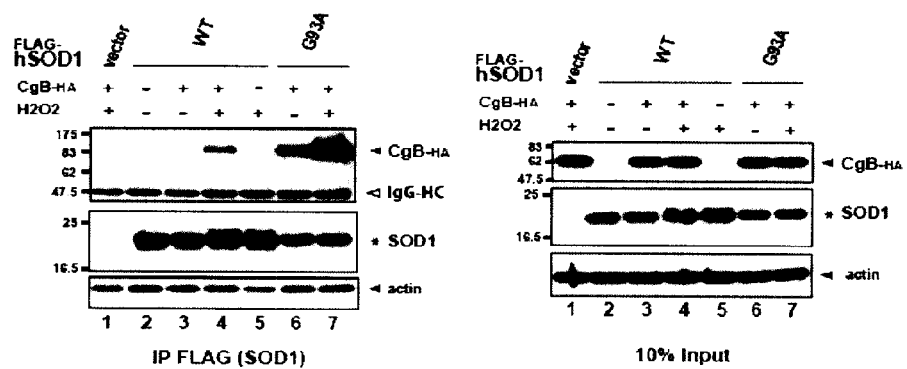

FIGURE 13
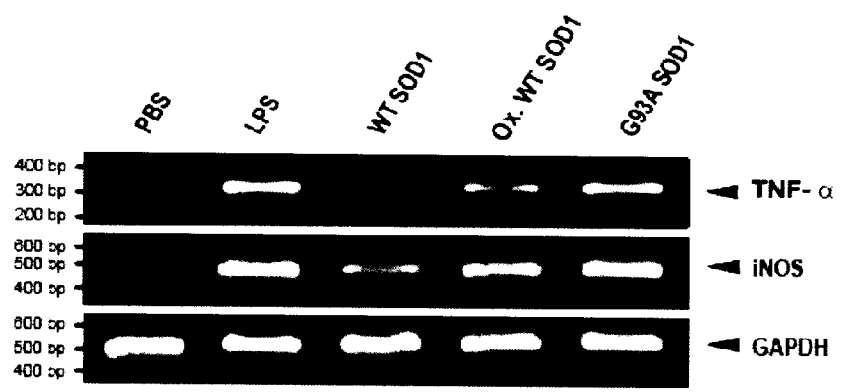
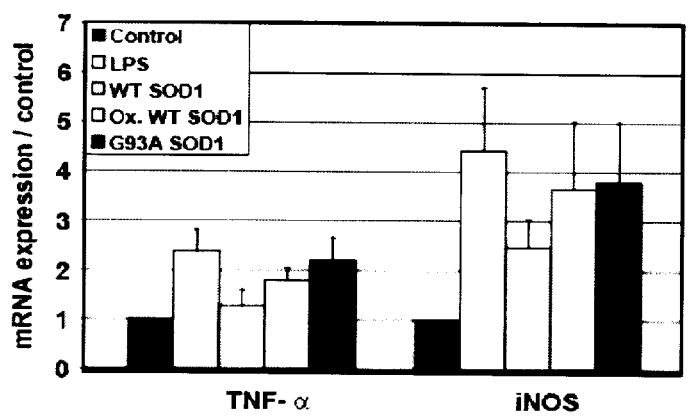

FIGURE 14
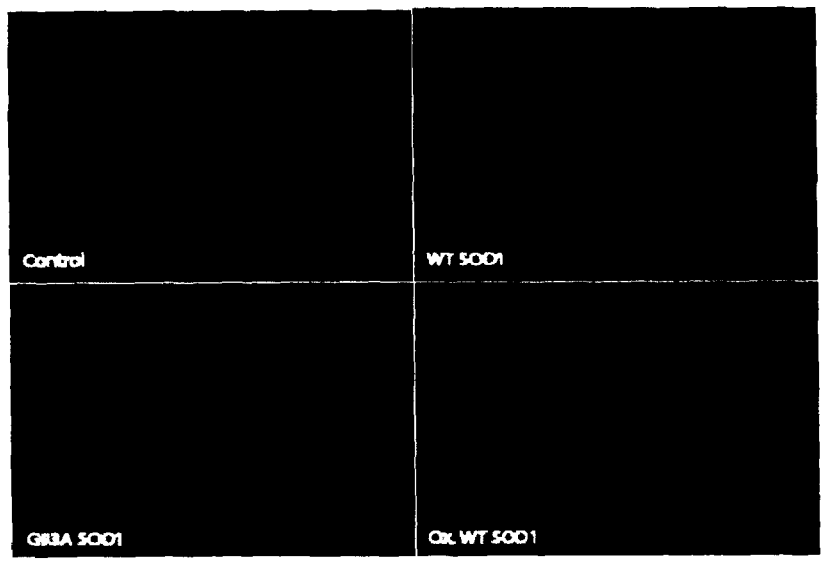
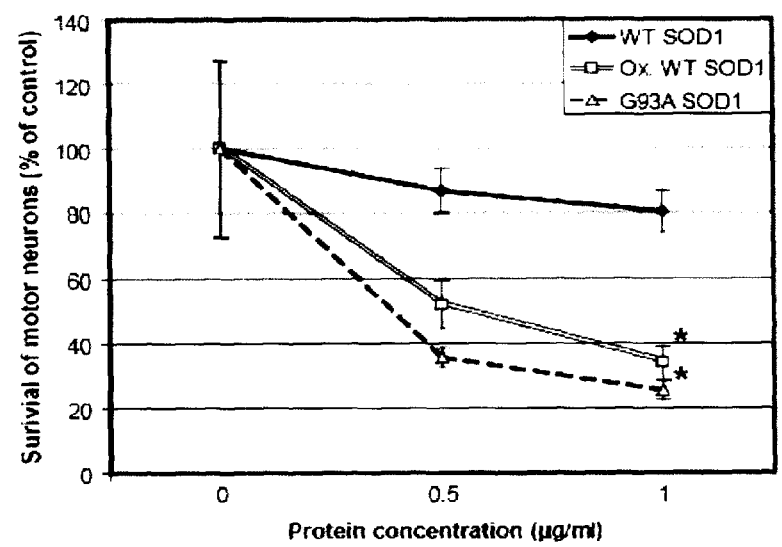

FIGURE 15
C4F6 for mutant-specific
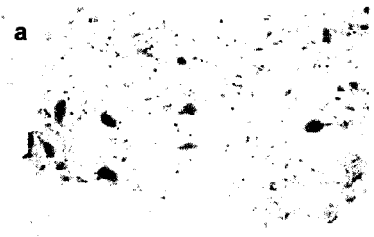
J2429 (human WT SOD1 x 200)
G93A high copy vacuoles (x 400)
J2429 (human WT SOD1 x 400)
G37R (x 400)
control (no Ab)
J2429 (human WT SOD1 x 200)
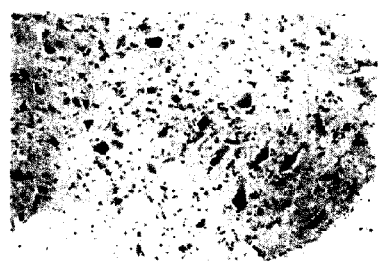
G37R (x 200)

FIGURE 18
D3H5 for both WT and mutants
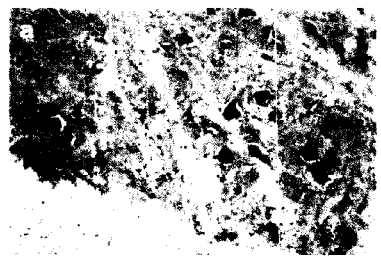
J2429 (human WT SOD1 x 200)
G93A high copy vacuoles (x 400)
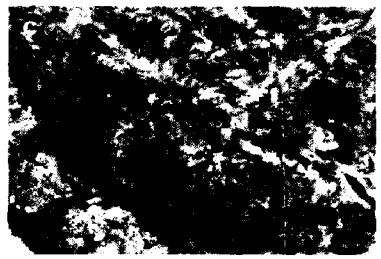
G37R (x 400)
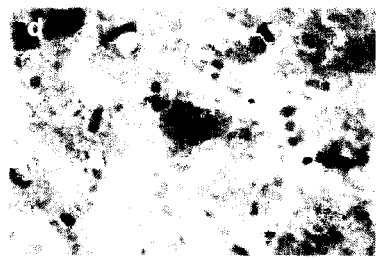
G37R inclusion (x 630)
control (no Ab)
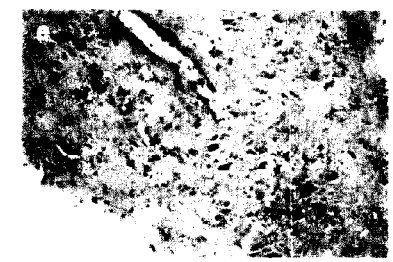
J2429 (human WT SOD1 x 200)
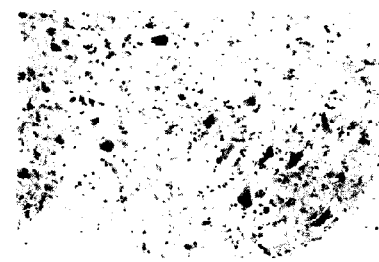
G37R (x 200)

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial sequence
<220> FEATURE:
<223> OTHER INFORMATION: PCR primer for TNF-alpha

<400> SEQUENCE: 1
tcagtgagac cactgcaatg                                                    20

<210> SEQ ID NO 2
<211> LENGTH: 20
<212> TYPE: DNA
<213> ORGANISM: Artificial sequence
<220> FEATURE:
<223> OTHER INFORMATION: PCR primer for TNF-alpha

<400> SEQUENCE: 2
gtggagtgag actttggatg                                                    20

<210> SEQ ID NO 3
<211> LENGTH: 19
<212> TYPE: DNA
<213> ORGANISM: Artificial sequence
<220> FEATURE:
<223> OTHER INFORMATION: PCR primer for iNOS

<400> SEQUENCE: 3
ccttgtgtca gccctcaga                                                     19

<210> SEQ ID NO 4
<211> LENGTH: 21
<212> TYPE: DNA
<213> ORGANISM: Artificial sequence
<220> FEATURE:
<223> OTHER INFORMATION: PCR primer for iNOS

<400> SEQUENCE: 4
cactctcttg cggaccatct c                                                  21

<210> SEQ ID NO 5
<211> LENGTH: 19
<212> TYPE: DNA
<213> ORGANISM: Artificial sequence
<220> FEATURE:
<223> OTHER INFORMATION: PCR primer for GAPDH

<400> SEQUENCE: 5
ggcattgtgg aagggctca                                                     19

<210> SEQ ID NO 6
<211> LENGTH: 19
<212> TYPE: DNA
<213> ORGANISM: Artificial sequence
<220> FEATURE:
<223> OTHER INFORMATION: PCR primer for GAPDH

<400> SEQUENCE: 6
tccaccaccc tgttgctgt                                                     19

<210> SEQ ID NO 7
<211> LENGTH: 154
<212> TYPE: PRT
<213> ORGANISM: Homo sapiens
```

<400> SEQUENCE: 7

```
Met Ala Thr Lys Ala Val Cys Val Leu Lys Gly Asp Gly Pro Val Gln
1               5                  10                  15
Gly Ile Ile Asn Phe Glu Gln Lys Glu Ser Asn Gly Pro Val Lys Val
            20                  25                  30
Trp Gly Ser Ile Lys Gly Leu Thr Glu Gly Leu His Gly Phe His Val
        35                  40                  45
His Glu Phe Gly Asp Asn Thr Ala Gly Cys Thr Ser Ala Gly Pro His
    50                  55                  60
Phe Asn Pro Leu Ser Arg Lys His Gly Pro Lys Asp Glu Glu Arg
65                  70                  75                  80
His Val Gly Asp Leu Gly Asn Val Thr Ala Asp Lys Asp Gly Val Ala
                85                  90                  95
Asp Val Ser Ile Glu Asp Ser Val Ile Ser Leu Ser Gly Asp His Cys
            100                 105                 110
Ile Ile Gly Arg Thr Leu Val Val His Glu Lys Ala Asp Asp Leu Gly
        115                 120                 125
Lys Gly Gly Asn Glu Glu Ser Thr Lys Thr Gly Asn Ala Gly Ser Arg
    130                 135                 140
Leu Ala Cys Gly Val Ile Gly Ile Ala Gln
145                 150
```

<210> SEQ ID NO 8
<211> LENGTH: 981
<212> TYPE: DNA
<213> ORGANISM: Homo sapiens

<400> SEQUENCE: 8

```
gtttggggcc agagtgggcg aggcgcggag gtctggccta taaagtagtc gcggagacgg      60
ggtgctggtt tgcgtcgtag tctcctgcag cgtctgggt ttccgttgca gtcctcggaa      120
ccaggacctc ggcgtggcct agcgagttat ggcgacgaag gccgtgtgcg tgctgaaggg     180
cgacggccca gtgcagggca tcatcaattt cgagcagaag gaaagtaatg gaccagtgaa     240
ggtgtgggga agcattaaag gactgactga aggcctgcat ggattccatg ttcatgagtt     300
tggagataat acagcaggct gtaccagtgc aggtcctcac tttaatcctc tatccagaaa     360
acacggtggg ccaaaggatg aagagaggca tgttggagac ttgggcaatg tgactgctga     420
caaagatggt gtggccgatg tgtctattga agattctgtg atctcactct caggagacca     480
ttgcatcatt ggccgcacac tggtggtcca tgaaaaagca gatgacttgg gcaaaggtgg     540
aaatgaagaa agtacaaaga caggaaacgc tggaagtcgt ttggcttgtg gtgtaattgg     600
gatcgcccaa taaacattcc cttggatgta gtctgaggcc ccttaactca tctgttatcc     660
tgctagctgt agaaatgtat cctgataaac attaaacact gtaatcttaa aagtgtaatt     720
gtgtgacttt ttcagagttg ctttaaagta cctgtagtga gaaactgatt tatgatcact     780
tggaagattt gtatagtttt ataaaactca gttaaaatgt ctgtttcaat gacctgtatt     840
ttgccagact taaatcacag atgggtatta aacttgtcag aatttctttg tcattcaagc     900
ctgtgaataa aaaccctgta tggcacttat tatgaggcta ttaaaagaat ccaaattcaa     960
actaaaaaaa aaaaaaaaaa a                                               981
```

ANTIBODIES AND THEIR USE IN THE TREATMENT, PREVENTION AND DIAGNOSIS OF A DISEASE ASSOCIATED WITH SOD1 ABNORMALITIES

FIELD OF THE INVENTION

The present invention relates to the field of neurodegenerative diseases associated with SOD1 abnormalities, such as amyotrophic lateral sclerosis (ALS). More specifically, the present invention relates to monoclonal antibodies and their use in compositions and methods for preventing, treating and/or diagnosing such a neurodegenerative disease.

BACKGROUND OF THE INVENTION

A neurodegenerative disease is a disorder caused by the deterioration of certain nerve cells. Changes in these cells cause them to function abnormally, eventually bringing about their death.

Neurodegenerative diseases include familial and sporadic amyotrophic lateral sclerosis (FALS and ALS, respectively), familial and sporadic Parkinson's disease, Huntington's disease, familial and sporadic Alzheimer's disease, olivopontocerebellar atrophy, multiple system atrophy, progressive supranuclear palsy, diffuse lewy body disease, corticodentatonigral degeneration, progressive familial myoclonic epilepsy, strionigral degeneration, torsion dystonia, familial tremor, Gilles de la Tourette syndrome, and Hallervorden-Spatz disease. Most of the diseases are typified by onset during the middle adult years and lead to rapid degeneration of specific subsets of neurons within the neural system, ultimately resulting in premature death. There is no known cure nor is there an effective therapy to slow the progression for any of the stated diseases.

Amyotrophic lateral sclerosis (ALS) is a lethal neurodegenerative disease characterized by progressive muscle weakness during adulthood. Pathological hallmarks are represented by the massive loss of motor neurons together with astrocytosis and microgliosis in the motor cortex, brainstem and spinal cord. Generally, the onset is between the third and sixth decade, typically in the sixth decade. ALS is uniformly fatal, typically within five years. ALS may only be diagnosed when the patient begins to experience asymmetric limb weakness and fatigue, localized fasciculation in the upper limbs and/or spasticity in the legs which typifies onset.

In ALS, the neurons of the cerebral cortex and anterior horns of the spinal cord, together with their homologues in some of the motor nuclei of the brain stem, are affected. The class of neurons affected is highly specific; motor neurons for ocular motility and sphincteric motor neurons of the spinal cord remain unaffected until very late in the disease. Although death occasionally results shortly after the onset of the symptomatic disease, the disease generally ends with respiratory failure secondary to profound generalized and diaphragmatic weakness.

Approximately 10% of ALS cases are family related, the remainder ALS cases being diagnosed as sporadic (90%). The discovery a decade ago by Rosen et al. (1993, Nature, 362, 59-62) of missense mutations in the gene coding for the Cu/Zn superoxide dismutase 1 (SOD1) in subsets of familial cases directed most ALS research to elucidating the mechanism of SOD1-mediated disease. To date, 114 different mutations have been discovered in the SOD1 gene that account for ~20% of familial ALS cases.

The enzyme superoxide dismutase (SOD), catalyzes the dismutation of superoxide into oxygen and hydrogen peroxide. As such, it is an important antioxidant defense in nearly all cells exposed to oxygen. SOD is widely distributed in a living body of animals, plants or microorganisms. More specifically SOD1 is an abundant and ubiquitously expressed protein. Because of its normal function in catalyzing the conversion of superoxide anions to hydrogen peroxide, it was first thought that the toxicity of different SOD1 mutants could result from decreased free-radicals scavenging activity. However, different SOD1 mutants showed a remarkable degree of variation with respect to enzymatic activity. Mice expressing mutants SOD1 G93A (glycine substituted to alanine at position 93) or SOD1 G37R developed motor neuron disease despite elevation in SOD1 activity levels (Cleveland et al., 2001, Nat Rev Neurosc, 2, 806-819). Moreover, SOD1 knockout mice did not develop motor neuron disease (Reaume et al., 1996, Nat Genet, 13, 43-47). Gene disruption for the copper chaperone for SOD1 (CCS) that delivers copper to SOD1 catalytic site had no effect on disease progression in mutant SOD1 transgenic mice (Subramanian et al., 2002, Nat Neurosci, 5, 301-307). Finally, transgenic mice overexpressing a mutant form of SOD1 lacking two of the four histidine residues coordinating the binding of the Cu at the catalytic site still developed motor neurodegeneration despite a marked reduction in SOD1 activity (Wang et al., 2002, Neurobiol Dis, 10, 128-138). Overall, these studies with genetically altered mice indicate that SOD1 mutants cause motor neuron disease through the gain of new toxic properties that is independent of the enzymatic activity involving the copper catalytic site.

The most prevailing view is that the toxicity of SOD1 mutants is related to the propensity of mutant SOD1 to form noxious misfolded protein species and aggregates. Moreover, unlike wild type (WT) SOD1, extracellular mutant SOD1 proteins activate microglia and induce motor neuron death in culture (Urushitani et al., 2006, Nat Neurosci, 9, 108-118), a pathogenic pathway that would be in line with the notion that motor neuron death in mutant SOD1-linked ALS is not strictly cell-autonomous (Boillee et al., 2006, Science, 312, 1389-1392). Interestingly, the oxidation of WT SOD1 is a phenomenon that may promote its aggregation (Furukawa, et al., 2006, PNAS USA, 103, 7148-7153). Considering evidence of oxidative damage in sporadic ALS patients (Ihara et al., 2005, Neurol Res, 27, 105-108) and the abundance of SOD1 protein in cells, it seems plausible that SOD1 molecules might constitute targets of oxidative damage in sporadic ALS.

Since the discovery of genetic mutations in superoxide dismutase 1 (SOD1) in 20% of familial ALS patients and the development of excellent mouse models based on overexpression of ALS-linked SOD1 mutants, many pathogenic pathways to motor neuron death have been elucidated including protein misfolding and aggregation, proteasome impairment, inflammation, reactive oxygen species, excitotoxicity and mitochondrial dysfunction. Based on these hypotheses, multiple approaches for treatment have been tested in the ALS mice including pharmacological approaches and virus-mediated delivery of molecules.

U.S. Pat. No. 5,762,929 reports a pharmaceutical agent that may alleviate symptoms of motor neurons diseases such as amyotrophic lateral sclerosis by oral or parenteral administration. U.S. Pat. No. 5,780,489 reports a method for treating and alleviating the symptoms of amyotrophic lateral sclerosis by administering to a patient an effective amount of a non-cysteine glutathione precursor or a glutathione derivative. U.S. Pat. No. 6,420,429 reports the use of antioxidants for the treatment of diseases such as amyotrophic lateral sclerosis. U.S. Pat. No. 5,843,641; U.S. Pat. No. 5,849,290 and U.S.

Pat. No. 6,723,893 report the use of an effective amount of SOD protein or DNA encoding an SOD protein to treat neurodegenerative diseases, specifically amyotrophic lateral sclerosis (ALS). They also report a method of diagnosis of amyotrophic lateral sclerosis using the DNA encoding an SOD protein or a fragment thereof in a PCR reaction.

Although it is well known that SOD1 is a cytosolic protein without specific translocation sequence, there is emerging evidence that both normal and mutant SOD1 can be secreted through secretory pathways (Urushitani, et al., 2006, Nature Neurosci, 9, 108-118). Furthermore, Urushitani, et al. (2006) discovered that extracellular SOD1 mutant can trigger microgliosis and death of motor neurons in culture suggesting a pathogenic mechanism based on toxicity of secreted SOD1 mutant proteins.

There is thus need for new agents, such as monoclonal antibodies which are efficient for the treatment, prevention and/or diagnosis of diseases associated with SOD1 abnormalities.

SUMMARY OF THE INVENTION

An object of the present invention is to provide tools for treating and/or diagnosing SOD1 associated diseases that satisfy the above-mentioned need.

That object of the present invention is achieved by providing antibodies which specifically bind to an abnormal superoxide dismutase 1 (SOD1) and which neutralize the pathologic effect of the abnormal SOD1 when administered to an animal. Preferably the antibodies of the invention are monoclonal antibodies.

More specifically, the monoclonal antibodies of the invention are preferably produced by hybridoma cell lines deposited with the International Depositary Authority of Canada on Aug. 29, 2006 under accession numbers ADI-290806-01, ADI-290806-02 and ADI-290806-03. The address for the International Depositary Authority of Canada is 1015 Arlington Street, Winnipeg, Canada, R3E 3R2.

Another aspect of the invention concerns a composition for preventing and/or treating a disease associated with SOD1 abnormalities in an animal, comprising a pharmaceutically acceptable carrier and at least an antibody according to the invention.

The present invention further concerns the use of at least an antibody of the invention for preventing and/or treating a disease associated with SOD1 abnormalities in an animal or the use of an antibody of the invention in the preparation of a composition for preventing and/or treating a disease associated with SOD1 abnormalities in an animal.

Another aspect of the invention is the use of at least one monoclonal antibody of the invention for the diagnosis of a disease associated with SOD1 abnormalities in an animal, or for the preparation of a composition for the diagnosis of a disease associated with SOD1 abnormalities in an animal.

Yet another aspect of the invention concerns a kit for diagnosis of a disease associated with SOD1 abnormalities in an animal. The kit comprises a container, which contains at least one monoclonal antibody according to the present invention.

Yet another aspect of the invention is a kit for treatment or prevention of a disease associated with SOD1 abnormalities in an animal. The kit comprises a container which contains at least an antibody of the invention.

Yet another aspect of the invention is a method for preventing and/or treating a disease associated with SOD1 abnormalities in an animal, said method comprising the step of administering an effective amount of a composition according to the invention.

Other objects and advantages of the present invention will be apparent upon reading the following non-restrictive detailed description, made with reference to the accompanying drawings.

b. Rotarod analysis of the vaccinated mice with early immunization protocol. The time on the rotarod was determined for G37R SOD1 mice injected with rec G93A-adjuvant (N=8) or with saline-adjuvant (N=7). The vaccination significantly improved motor performance (P<0.0001 by post-hoc test).

c. Effect of immunization on delay of onset (as defined by loss of 30% of motor performance) in G37R SOD1 mice immunized with rec G93A-adjuvant or with saline-adjuvant. P=0.0011 by log rank test.

d. Immunization increases the lifespan of G37R SOD1 mice. Kaplan-Meier curve for survival. N=8 for rec G93A-treated mice and N=7 for saline-injected mice. P<0.0001 by log-rank test.

e. Increased number of remaining motor neurons in vaccinated mice at end stage of disease. After staining of the sections with Toluidine blue, motor neurons were counted in 4 sections from 4 mice in each group. *P<0.01 by student's t-test.

f. Immunohistochemistry of the spinal cord of end stage G37R SOD1 transgenic mice immunized with recombinant G93A SOD1 protein (upper) or saline (lower), using antibodies against NeuN.

FIG. 2 (a-e)

a. Immunohistochemistry of spinal cord from immunized mice using anti-Mac2 antibody. Note that more prominent Mac2 staining in reactive microglia of mouse vaccinated with recG93A SOD1 (left two panels).

(b.-e.) Increased IgG staining and microgliosis in spinal cord of vaccinated ALS mice. The spinal cord sections of G37R SOD1 transgenic mice from vaccinated or saline/adjuvant-injected group were treated with rat monoclonal anti-Mac2 antibody followed by Alexa 488-conjugated anti-rat IgG (left column), together with Alexa 594-conjugated anti-mouse IgG to detect endogenous IgG (middle column). For each dye, the photograph was taken under fixed conditions. Note the enhanced Mac2 and IgG signals in vaccinated G37R SOD1 mice. Scale bar=50 μm.

Figure 3:
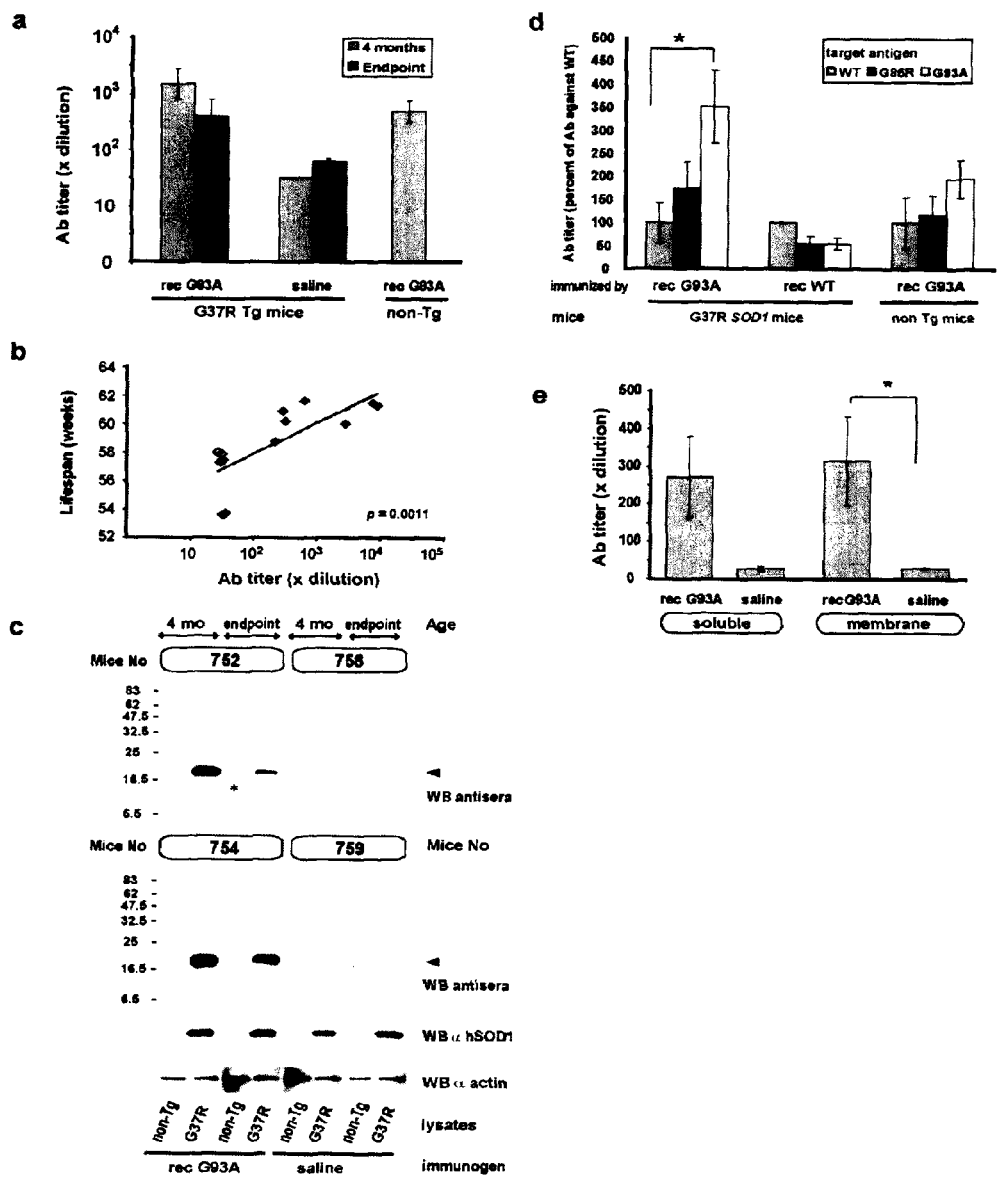

FIG. 3 (a-e) shows antibody titers correlate with the lifespan of vaccinated mice a. Antibody titration of the sera from immunized mice using enzyme-linked immunosorbent assay (ELISA). N=7 for rec G93A-treated G37R SOD1 mice. N=6 for saline-injected mice. Sera from mice at 4 months old and at end point were tested. N=4 for rec G93A-treated non-transgenic littermate mice (only at 4 months old).

b. Positive correlation between anti-human SOD1 titer and lifespan in immunized mice. The value from ELISA for anti-human SOD1 titer at 4 months old and the lifespan (weeks) was plotted on scatter diagram (N=7 for recombinant human SOD1-treated group, N=6 for saline-injected group. P=0.0011 analyzed by Spearman's rho test.

c. Western blot analysis shows that antisera from mice vaccinated with rec G93A SOD1 detect human G37R SOD1 mutant. The sera from two different mice from each group, mice 752 and 754 from the group vaccinated with rec G93A SOD1 and mice 758 and 759 from saline-adjuvant injected group, were reacted with spinal cord lysates from G37R SOD1 mice and form non-transgenic littermates (WB antisera). The arrowhead indicates G37R SOD1 and the asterisk indicates mouse endogenous SOD1. The membranes were reblotted with commercially available antibody against human SOD1 (WB α hSOD1) and actin (WB α actin).

d. Different reactivity of antisera from immunized mice against WT or mutant SOD1 proteins. Antibody titers against metallated recombinant human WT, G85R or G93A SOD1 metallated protein were determined by ELISA. N=3 from each group consisting of G37R SOD1 mice vaccinated with rec G93A SOD1 or with rec WT SOD1, or non-transgenic mice vaccinated with rec G93A SOD1. The data are presented as percent of the titer as compared to that against rec WT SOD1 in each mice group (averaged±sem). *P<0.05 by one way ANOVA with Bonferroni's method.

e. ELISA analysis for antibody titration of the spinal cord lysates from vaccinated mice. Spinal cord lysates from mice injected with rec G93A SOD1 (N=3) or with saline-adjuvant (N=3) at 7 months old were subcellularly fractionated into detergent-free buffer-soluble (soluble) and -insoluble (membrane) fractions before ELISA assay. *P<0.05 by one way ANOVA.

Figure 4:
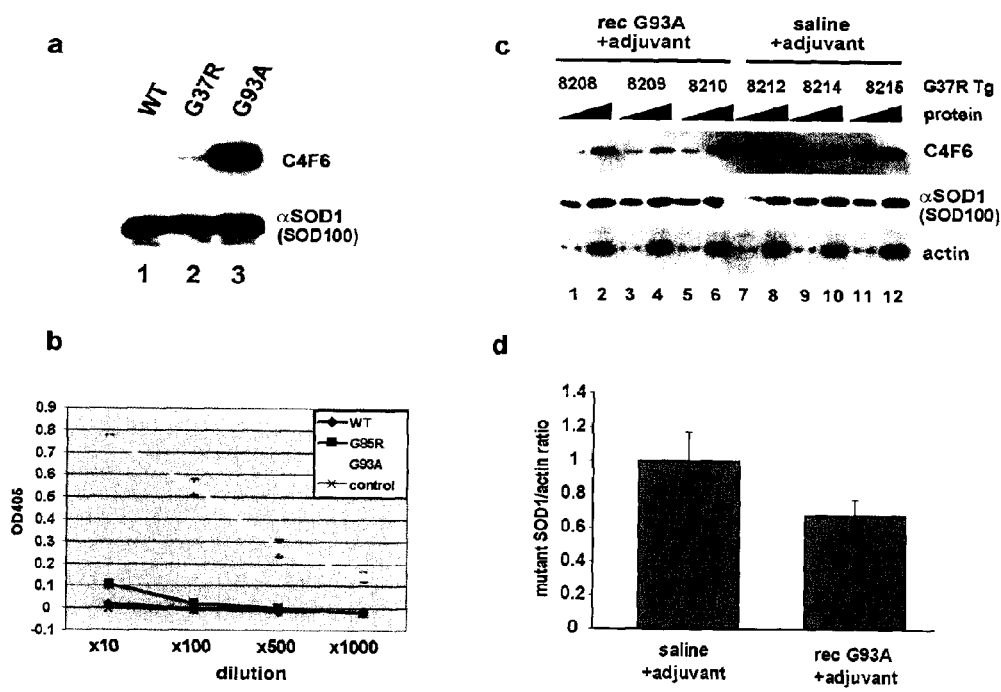

FIG. 4 (*a-d*) shows clearance of mutant SOD1 species in the spinal cord by vaccination with a preferred monoclonal antibody of the invention a. Western blot analysis showing that one of the preferred monoclonal antibody of the invention namely the C4F6 monoclonal antibody recognizes the mutant SOD1 forms (G37R and G93A) but poorly the WT SOD1 from spinal cord extracts of transgenic mice.

b. ELISA analysis showing that the C4F6 monoclonal detects the G85R metallated SOD1 protein but not the WT metallated SOD1 recombinant protein.

c. Western blotting analysis of spinal cord extracts showing lower amount of mutant SOD1 species detected by C4F6 antibody in vaccinated mice as compared to adjuvant-saline control mice. Five and ten micrograms of protein from each mouse were loaded onto each well for Western analysis. Three mice from both vaccinated and saline-injected mice were analyzed.

d. Densitometric analysis of the Western blot data in c. The average value of control group was standardized into one. Data shows mean±s.e.m. (N=3 from each group).

Figure 5:
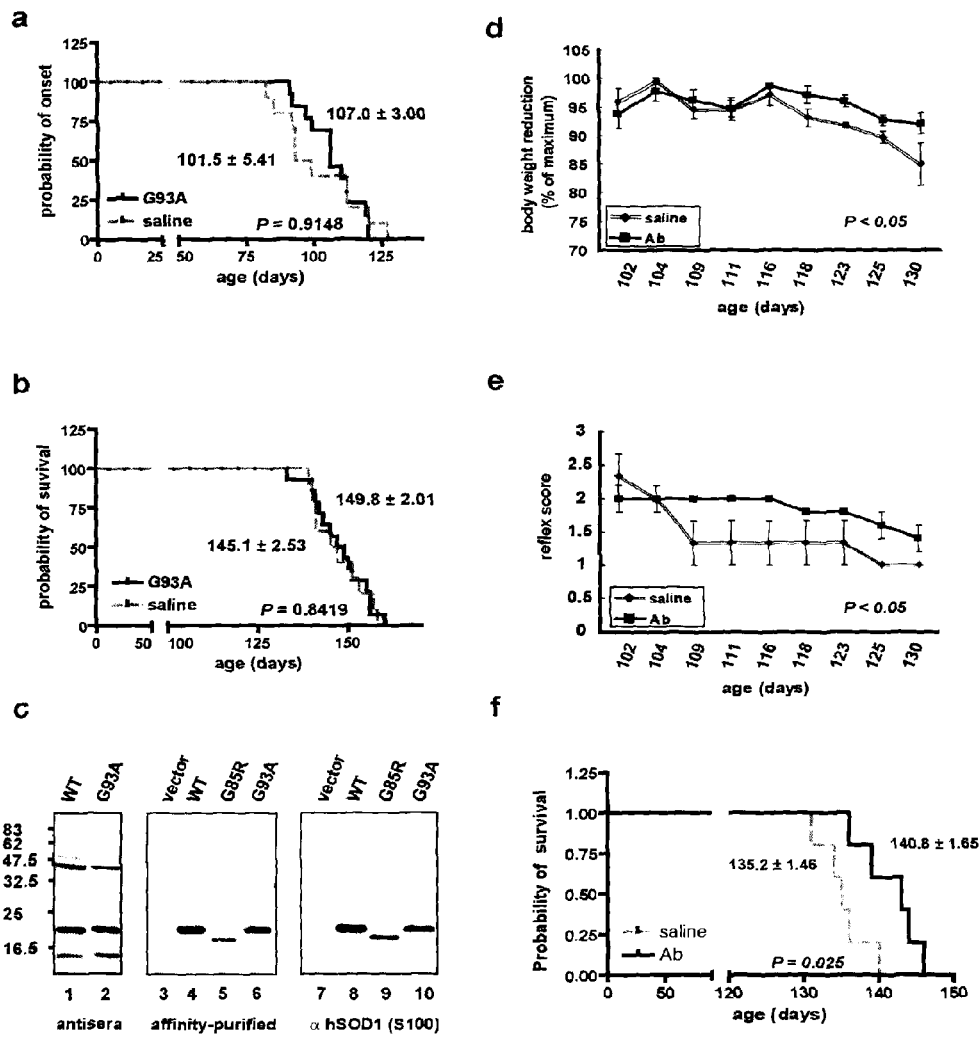

FIG. 5 (*a-f*) shows the effects of active or passive immunization in G93A SOD1 mice with extreme levels of mutant SOD1 protein a, b. Limited effect of active immunization on probability of disease onset (a) and survival (b) of G93AGur SOD1 mice as shown by Kaplan-Meier curve. Mice were vaccinated with the same protocol used for the G37R SOD1 mice. N=12 for rec G93A-treated mice and N=8 for saline-injected mice. Data was analyzed by log-rank test.

c-e. Significant effect of passive immunization in G93A SOD1 mice. Mice were subjected to intraventricular infusion of anti-SOD1 antibody (Ab, N=5) or control saline (N=5) starting at 85 days old. c, Western blotting demonstrating anti-G93A SOD1 antibody affinity-purified from antisera of immunized mice. d-f, Passive immunization with anti-human G93A SOD1 antibody alleviated disease symptoms as monitored by body weight (d) and hindlimb reflex score (e). The results are statistically significant (p<0.05, two-way ANOVA). f. Passive immunization prolonged the lifespan of G93A SOD1 mice significantly compared with saline-injected mice. (P=0.025 by Kaplan-Meier survival test, log-rank test and student's t-test).

Figure 6:
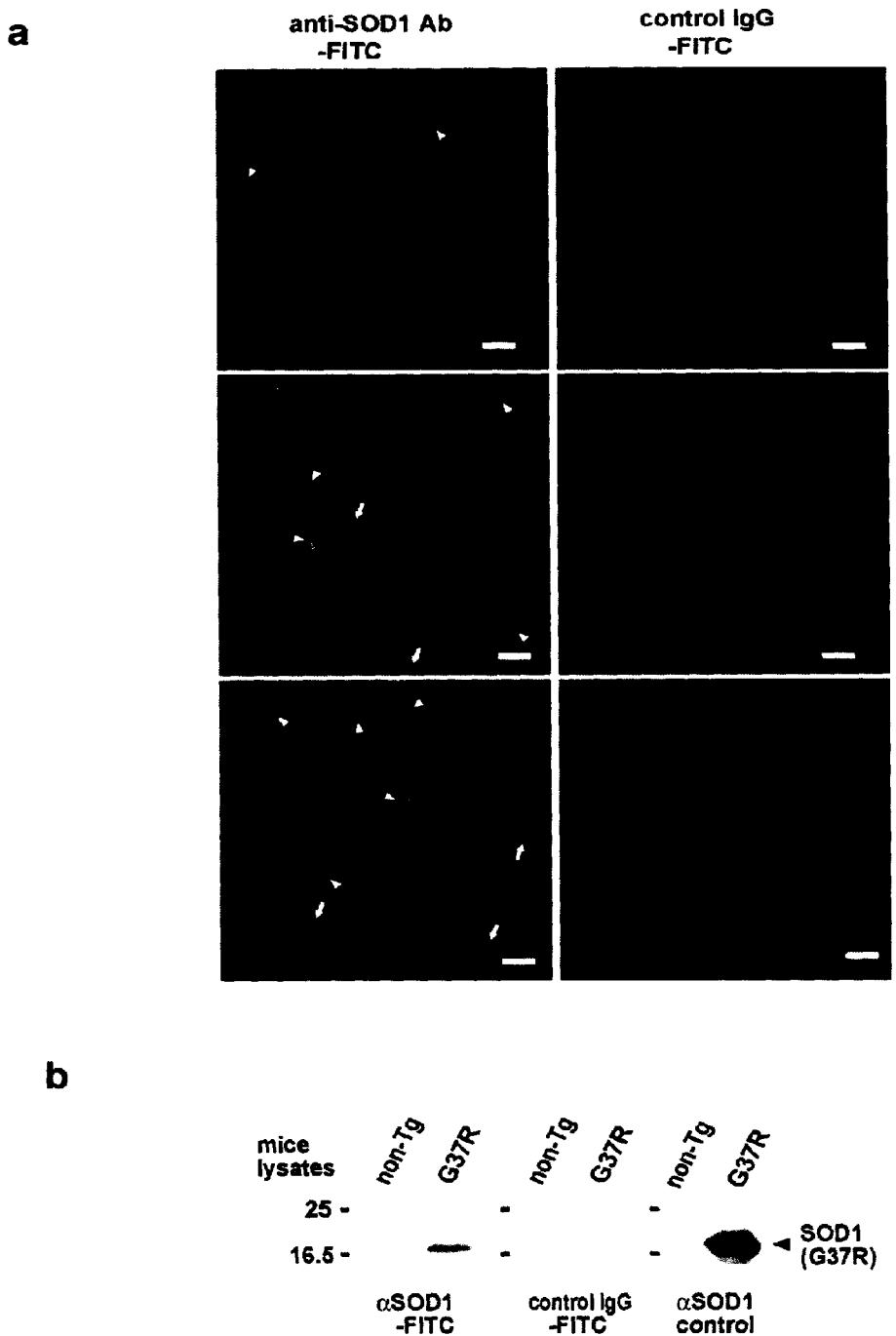

FIG. 6 (*a-b*) shows the anti-human SOD1 antibodies infused through osmotic mini-pump can penetrate into lumbar spinal cord and still active at 16 days after pump installment Rabbit polyclonal anti-human SOD1 antibodies or control IgG were conjugated with FITC and used for intraventricular Infusion via osmotic mini-pump for G93A SOD1 mice (100 days old).

a. Immunofluorescent analysis of lumbar spinal cord of the G93A SOD1 mice treated with intraventricular infusion of FITC-conjugated anti-human SOD1 antibodies (left column) or control IgG (right column). Green, FITC-conjugated antibodies or control IgG; red, anti-NeuN; blue, anti-Mac2 antibodies. FITC-conjugated SOD1 antibodies were detected in the vicinity of spinal neurons (arrowheads), and microglia (arrows).

b. Western blot of spinal cord extracts using FITC-conjugated anti-human SOD1 antibodies or control IgG from samples at 16 days after pump installment. Fresh antibody against human SOD1 was used as control. This confirms the reactivity of the residual antibody in the pump after 16 days of installment.

Figure 7:
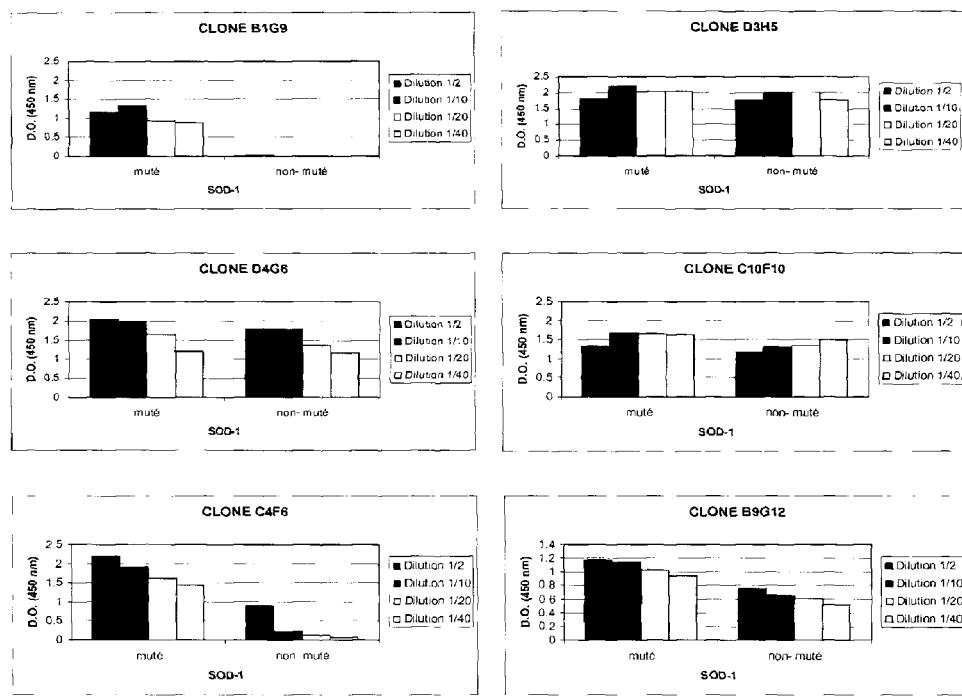

FIG. 7 shows the ELISA results of the affinity of the preferred monoclonal antibodies of the invention to the mutant SOD1 and WT SOD1.

FIG. 8 shows the amino acid sequence of the superoxide dismutase 1 namely SEQ ID NO 7.

FIG. 9 shows the nucleic acid sequence of the superoxide dismutase 1 namely SEQ ID NO 8.

FIG. 10 (A-B) shows that oxidation induces aggregation of WT SOC1 in vitro

A. Formation of SOD1 aggregate species by treatment with hydrogen peroxide ($H_2O_2$). Bacterially purified recombinant SOD1 proteins (1 mg/ml, WT, G85R and G93A) were incubated in a solution containing 1 mM $H_2O_2$ for 30 min at 37° C. After addition of 50 U/ml catalase to stop the reaction, protein samples were analyzed by Western blotting using anti-human SOD1 antibody. Note that, upon $H_2O_2$ treatment, WT SOD1 yielded high molecular aggregates like those in samples of mutant SOD1 proteins. The arrows indicate SOD1 fragments whose sequences were confirmed by mass spectrometry (data not shown). The asterisk symbol marks the catalase added to scavenge $H_2O_2$.

B. Oxidation-derived aggregation and fragments of SOD1 showed altered solubility in PBS. After the treatment of recombinant SOD1 protein by $H_2O_2$, proteins were dialyzed against PBS and subsequently ultracentrifuged (105,000 g×1 hr). Supernatants or pellets were analyzed by Western blotting using anti-human SOD1 antibody. Note that various patterns of fragmentation and possible complexes involving SOD1 fragments appeared as indicated by arrows.

Figure 11:
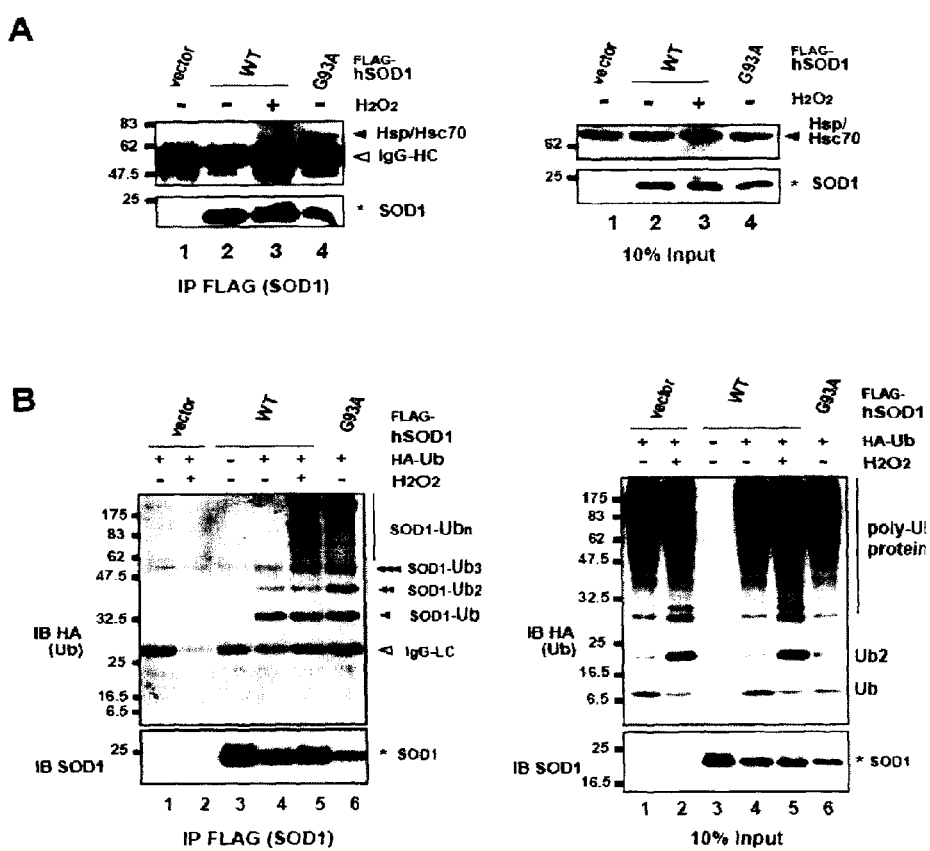

FIG. 11 (A-B) shows induction of WT SOD1 misfolding by oxidative stress in vitro A. Interactions of Hsp/Hsc70 with oxidized WT SOD1 or with mutant SOD1 in vivo. Neuro2a cells were transiently transfected with FLAG-tagged hSOD1 (WT and G93A; 2 μg/well) in culture plates. At 24 hrs post-transfection, the cells incubated for 45 min with buffer containing 1.5 mM $H_2O_2$. The lysates were immunoprecipitated with anti-FLAG affinity gel and blots were probed with anti-SOD1 or anti-Hsp/Hsc70 antibodies. Empty arrowhead indicates IgG heavy chain. The black arrowhead points to Hsp/Hsc70 protein that was co-immunoprecipitated with oxidized WT SOD1 or with mutant SOD1.

B. Multi-ubiquitin conjugation with oxidized WT SOD1 protein. HA-Ubiquitin (HA-Ub; 1 μg/well) was co-transfected with FLAG-hSOD1 followed by the experiment described in A. The immunoprecipitates with anti-FLAG affinity gel were resolved on 12.5% SDS-polyacrylamide gel. Immunoprecipitates (left panel) and 10% input lysates (right panel) were analyzed by Western blotting using anti-SOD1 or anti-HA antibody. Empty arrowhead indicates IgG light chain. Multi-ubiquitin conjugation occurred with mutant SOD1 as well as with oxidized WT SOD1 species.

FIG. 12 (A-B) shows the interaction of oxidized WT SOD1 or mutant SOD1 with chromogranin B A. Western blot analysis of the subcellular distribution of human SOD1 in transfected Neuro2a cells. At 24 hrs after transfection with hSOD1-FLAG (WT and G93A mutant), cells were treated with 1.5 mM $H_2O_2$ for 45 min before harvesting. Cells were subsequently processed to subcellular fractionation resulting into cytosolic (lane 1-4), heavy membrane (5-8) and light membrane fractions (9-12). The distribution of human SOD1 and CgB was analyzed. Akt-kinase, COX-IV, TGN-38 and syntaxin-1 were the markers for cytosol, mitochondria, microsome and membrane components, respectively.

B. Neuro2a cells were transiently transfected with hSOD1-FLAG (WT and G93A at 1 μg/well) and mouse HA-CgB (1 μg/well). At 24 hrs after transfection, the cells were exposed to 1.5 mM $H_2O_2$ for 45 min. Then, cell lysates were immunoprecipitated with anti-FLAG affinity gel. The immunoprecipitates and 10% input were analyzed by Western blotting using anti-SOD1 or anti-HA antibodies (12.5% SDS-acrylamide gel).

FIG. 13 (A-B) shows the oxidized WT SOD1 and mutant SOD1 are equally toxic to cultured motor neurons Microglial BV2 cells were exposed to $H_2O_2$-treated or intact WT SOD1 (Ox-WT SOD1 or WT SOD1 at 10 μg/ml), non-oxidized G93A SOD1 (10 μg/ml), LPS (10 μg/ml) or PBS for control for 24 hours at 37° C. Total RNA was analyzed by semi-quantitative reverse transcriptase PCR (RT-PCR) using primer pairs for Tumor necrosis factor alpha (TNF-α), inducible Nitric oxide synthase (iNOS) and Glyceraldehyde-3-phosphate dehydrogenase (GAPDH). A. Representative data of RT-PCR. B. Densitometric values normalized with GAPDH and expression ratio obtained by comparing with the PBS control (bottom; mean±S.E.M.).

FIG. 14 (A-B) shows the oxidized WT SOD1 and mutant SOD1 are equally toxic to cultured motor neurons Dissociated cultures at 12 days in vitro from E13 embryonic mouse spinal cords were exposed to $H_2O_2$-treated, non-treated recombinant WT SOD1 (Ox. WT SOD1, WT SOD1) or to G93A SOD1 (0.5 and 1.0 μg/ml) for 24 hours at 37° C. Cultures were fixed and labelled with anti-non-phosphorylated neurofilament H (SMI32). A. Micrographs of the primary spinal cord cultures treated with control PBS (top left). WT SOD1 (top right), $H_2O_2$-reacted WT SOD1 (bottom right) and G93A SOD1 (bottom left). B. Motor neuron survival after the treatment. The number of large SMI32-positive neurons as determined and expressed as % of control. The viability of motor neurons exposed to oxidized WT SOD1 or G93A SOD1 was significantly less than that of control cultures or cultures treated with intact WT SOD1. Data represent mean±SEM (Standard Error of Mean). n=3 or 4. Data was estimated by analysis of variance (ANOVA, $P<0.05$).

FIG. 15 (a-f) shows the immunohistochemistry results using spinal cord sections from human SOD1 transgenic mice Staining with clone C4F6, preferentially recognizing SOD1 mutants. Spinal cord slice (25 μm thickness) obtained from presymptomatic mutant SOD1 transgenic mice (G37R and G93A) or human WT transgenic mice were stained using a preferred monoclonal antibody of the invention, namely C4F6, followed by biotinylated $2^{nd}$ antibody and avidin-biotin complex system (Vectastain). Diaminobenzidine (DAB) was used as a chromogen. Antibody was obtained from supernatant of hybridoma culture medium (1:500). e and f are negative control without $1^{st}$ antibody.

Figure 16:
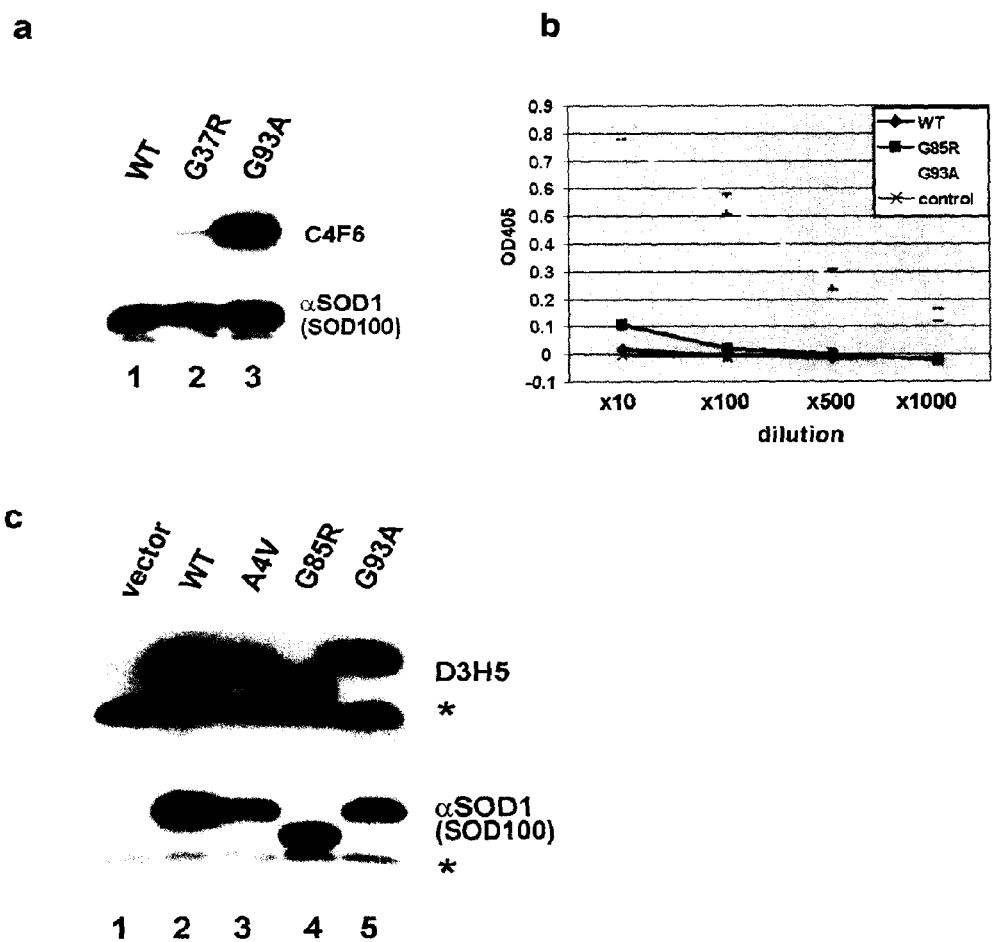

FIG. 16 (a-c) shows western blotting analysis using preferred monoclonal antibodies of the invention a. Western blotting analysis showing a preferred monoclonal antibody of the invention, namely C4F6, recognizes G37R SOD1 more than WT SOD1 from human SOD1 transgenic mice. As a control, rabbit polyclonal anti-human SOD1 antibody (S100, StressGen) was used.

b. ELISA analysis showing C4F6 antibody reacts against G85R metallated SOD1 protein than WT metallated recombinant protein.

c. Another preferred monoclonal antibody of the invention, namely D3H5, recognizes WT and various mutant SOD1 proteins. Western blotting of mouse neuroblastoma cell-line neuro2a cells, overexpression of human SOD1 (WT, A4V, G85R and G93A) or vector control. Cell lysates were analyzed by Western blotting with the preferred monoclonal antibody D3H5 recognizing both WT and mutant SOD1. S100 was used as a control.

Figure 17:
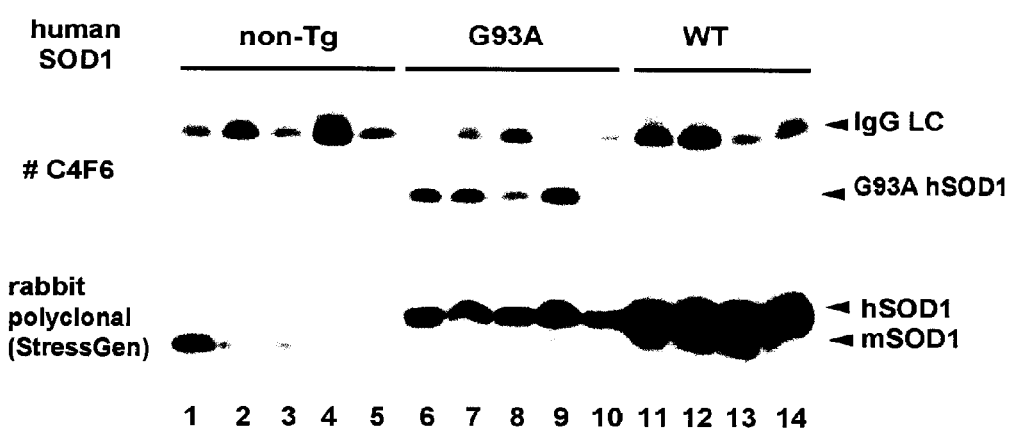

FIG. 17 shows the detection of human SOD1 Tg mice with a preferred monoclonal antibody of the invention, namely the C4F6.

Blood (50~100 microL/mouse) taken from mice was transferred to EDTA-treated sampling tube.

After centrifugation for 15 min at 1000×g at 4° C., the pellet was incubated in 10 mM Tris-HCl (pH 7.4) for 1 hr on ice. Samples were centrifuged for 20 min at 20,000×g at 4° C., and then supernatant was collected and boiled in SDS-sampling buffer for 5 min.

The figure shows Western blotting data using a preferred monoclonal antibody of the invention namely the C4F6 mouse monoclonal antibody (upper panel) and commercially available rabbit polyclonal anti-human SOD1 antibody (StressGen, Victoria, BC).

Each lane contains 10 micro G of proteins.

FIG. 18 (a-f) immunohistochemistry results using spinal cord sections from human SOD1 transgenic mice Staining with a monoclonal antibody of the invention, namely D3H5, recognizing both WT and mutant SOD1. Spinal cord slice (25 μm thickness) obtained from presymptomatic mutant SOD1 transgenic mice (G37R and G93A) or human WT transgenic mice were stained using mouse monoclonal anti-human SOD1 antibody (D3H5 clone), followed by biotinylated $2^{nd}$ antibody and avidin-biotin complex system (Vectastain). Diaminobenzidine (DAB) was used as a chromogen. Antibody was obtained from supernatant of hybridoma culture medium (1:500). e and f are negative control without $1^{st}$ antibody.

DETAILED DESCRIPTION OF THE INVENTION

In describing the present invention, the following terminology will be used in accordance with the definitions set out below:

As used therein, the disease associated with SOD1 abnormalities preferably refers to a neurodegenerative disease.

Neurodegenerative disease is a varied assortment of central nervous system disorders characterized by gradual and progressive loss of neural tissue. A non exhaustive list of neurodegenerative disease includes, but is not limited to Parkinson's disease, Alzheimer's disease, Huntington's disease, Hallervorden-Spatz disease, olivopontocerebellar atrophy, multiple system atrophy, progressive supranuclear palsy, diffuse lewy body disease, corticodentatonigral degeneration, progressive familial myoclonic epilepsy, strionigral degeneration, torsion dystonia, familial tremor, gilles de la tourette syndrome, and Hallervorden-Spatz disease, and amyotrophic lateral sclerosis (ALS) which is familial, sporadic typical, or atypical in nature.

"Humanized" forms of non-human (e.g., murine) antibodies are specific chimeric immunoglobulins, immunoglobulin chains or fragments thereof (such as Fv, Fab, Fab', F(ab')$_2$, or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat, or rabbit having the desired specificity, affinity, and capacity. In some instances, Fv framework residues of the human immunoglobulin are replaced by corresponding non-human residues. Furthermore, humanized antibodies can comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details see Jones et al., Nature 321:522 (1986); Reichmann et al., Nature 332:323 (1988); and Presta, Curr. Op. Struct. Biol. 2:593 (1992).

Wild type is the naturally-occurring, normal, non-mutated version of a gene or protein.

Abnormalities, abnormal: when referring to an abnormal SOD1 protein, means that the abnormal SOD1 protein has the same or substantially a similar amino acid sequence as the wild type SOD1 protein but has a different protein conformation from that of the wild type SOD1 protein and has a pathogenic activity. The pathogenic activity in this case is involved in the development of neurodegenerative diseases as defined above. By the term abnormal/abnormalities it is understood mutant, oxidized or aggregated SOD1 proteins.

The term "immunizing" or "immunization" as used herein, refers to the production of an immune response (humoral and/or cellular response) in a patient that protects (partially or totally) from the manifestations of disease. Immunizations may be either prophylactic or therapeutic in nature. Immunization may also be passive. Passive immunization therapy an impermanent form of acquired immunity in which antibodies against a disease are acquired naturally (as through the placenta to an unborn child) or artificially (as by injection of antiserum). It is a process in which individuals with advanced disease are infused with plasma rich in antibodies or also before the onset of the disease symptoms. The antibodies are the polyclonal or the monoclonal antibodies of the present invention. The passive immunization treatment thus involves the delivery of agents with established abnormal SOD1 immune reactivity (such as effector cells or antibodies, more specifically monoclonal antibodies) that can directly or indirectly mediate anti-abnormal SOD1 effects and do not necessarily depend on an intact host immune system.

As used herein, the term "animal" refers to any animal including humans, domestic and farm animals, and zoo, sports, or pet animals, such as dogs, horses, and cats. Preferably, the animal herein is human.

Diagnosis as used herein is the process of identifying a disease by its signs, symptoms and results of various diagnostic procedures. Diagnosis may be performed on biological samples taken from a subject, preferably an animal and more preferably a human. Such samples may be selected from, but are not limited to the following: blood plasma or serum, whole blood, urine, sputum, colonic effluent, cerebrospinal fluid, lymphatic fluid, bone marrow, tissue samples such as from a surgical biopsy or oral smear, or any other sample suspected of containing abnormal SOD1. Preferably the sample used for diagnosis is blood plasma or serum.

The term monoclonal antibody as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they can be synthesized by hybridoma culture, uncontaminated by other immunoglobulins.

1. The Antibodies and Compositions of the Invention

The inventors have found that immunization of animals with a mutant superoxide dismutase polypeptide which is the putative agent causing a neurodegenerative disease such as amyotrophic lateral sclerosis (ALS) allows to treat and/or to prevent such a disease.

The inventors have also showed for the first time that passive immunization with an antibody against mutant superoxide dismutase polypeptide allows to treat and/or to prevent such a disease.

Therefore, the present invention concerns antibodies which specifically bind to an abnormal superoxide dismutase 1 (SOD1). By abnormal superoxide dismutase 1 it is meant a superoxide dismutase 1 that may be mutated, oxidized, aggregated, or having an altered conformation and retaining a pathogenic activity.

The antibodies of the invention specifically bind to the abnormal SOD1 and neutralize its pathologic effect when they are administered to an animal, such as a human. The antibodies of the invention are produced as described in Example 2 below.

With respect to antibodies of the invention, the term "specifically binds to" refers to antibodies that bind with a relatively high affinity to one or more epitopes of the SOD1 polypeptide, but which do not substantially recognize and bind molecules other than the SOD1 polypeptides contemplated by the present invention. As used herein, the term "relatively high affinity" means a binding affinity between the antibody and the epitope of interest of at least $10^6$ M$^{-1}$, and preferably of at least about $10^7$ M$^{-1}$ and even more preferably $10^8$ M$^{-1}$ to $10^{10}$ M$^{-1}$. Determination of such affinity is preferably conducted under standard competitive binding immunoassay conditions, which is common knowledge to one skilled in the art.

In a preferred embodiment of the invention, the antibodies are monoclonal antibodies. Monoclonal antibodies of the invention are prepared as described in Example 1 below.

The present invention also concerns the hybridoma cell lines deposited with the International Depositary Authority of Canada on Aug. 29, 2006 under accession numbers ADI-290806-01, ADI-290806-02 and ADI-290806-03. In a most preferred embodiment, the monoclonal antibodies of the invention are the monoclonal antibodies produced by the hybridoma cell lines accessions ADI-290806-01, ADI-290806-02 and ADI-290806-03, and respectively named therein, B1G9, C4F6 and D3H5. As seen from FIG. 7 and table 3, the ELISA assays show that the monoclonal antibodies B1G9 has specific affinity with mutant SOD1 and no affinity to normal or wild type SOD1; C4F6 has a very strong affinity to mutant SOD1 and D3H5 has affinity to both types of SOD1 proteins. In specific immunohistochemistry assays, C4F6 has been shown to strongly detect SOD1 species in tissues (spinal cord and blood samples as seen from examples A and B) taken from transgenic mice expressing mutant SOD1 G93A. Thus, as can be appreciated, the monoclonal antibodies of the invention and more specifically C4F6, D3H5 and B1G9 strongly bind to abnormal SOD1 and more specifically to mutant SOD1 and can therefore be effective in passive immunization.

As may also be appreciated, the antibodies of the invention may be used to prepare a composition for preventing and/or treating a disease associated with SOD1 abnormalities in an animal. Therefore, the present invention also concerns a composition for preventing and/or treating a disease associated with SOD1 abnormalities in an animal. The composition comprises an anti-abnormal SOD1 antibody and a pharmaceutically acceptable carrier. As used herein, the term "pharmaceutically acceptable carrier" means a vehicle for containing the composition of the invention that can be injected into a host without adverse effects. Suitable pharmaceutically acceptable carriers known in the art include, but are not limited to, sterile water, saline, glucose, dextrose, or buffered solutions. Carriers may include auxiliary agents including, but not limited to, diluents, stabilizers (i.e., sugars and amino acids), preservatives, wetting agents, emulsifying agents, pH buffering agents, viscosity enhancing additives, colors and the like.

The antibody used in the composition of the invention preferably binds to the abnormal SOD1 protein and more preferably to the mutant SOD1 protein. The composition according to the invention, when administered to an animal, such as a human, will confer a therapeutic and/or protection effect to the animal against an abnormal SOD1 protein and more preferably against a mutant SOD1 protein. In a preferred embodiment of the invention, the antibody used in the composition of the invention is a polyclonal antibody prepared as in Example 2 or a monoclonal antibody prepared according to Example 1 below. In an even more preferred embodiment the monoclonal antibodies are C4F6, D3H5 and B1G9

2. Use of the Antibodies and Compositions of the Invention

According to another embodiment, the present invention provides for the use of at least one anti-abnormal SOD1 antibody for preventing and/or treating a disease associated with SOD1 abnormalities in an animal. According to yet another embodiment, the invention provides for the use of at least one anti-abnormal SOD1 antibody in the preparation of a composition for preventing and/or treating a disease associated with SOD1 abnormalities in an animal.

In a preferred embodiment of the invention, the at least one anti-abnormal SOD1 antibody is a polyclonal or a monoclonal antibody and more preferably a monoclonal antibody. In an even more preferred embodiment of the invention the antibody is a monoclonal antibody and preferably yet C4F6, D3H5 and/or B1G9.

The amount of anti-SOD antibodies present in the composition of the invention is preferably a therapeutically effective amount. A therapeutically effective amount of anti-SOD antibodies present in the composition of the invention is the amount necessary to allow the same to perform their biological role without causing overly negative effects in the host to which the composition is administered. The exact amount of anti-SOD1 antibodies present in the composition of the invention to be used and the composition to be administered will vary according to factors such as the type of condition being treated, the age and size of the animal to be treated, the mode of administration, as well as the other ingredients in the composition. The composition of the invention may be in the form of liquid solutions or suspensions; for oral administration, formulations may be in the form of tablets or capsules; and for intranasal formulations, in the form of powders, nasal drops, or aerosols.

The antibodies and or the composition of the invention are used to treat or prevent a disease associated with SOD1 abnormalities in an animal, such as a human.

As used herein, the terms "prevent, preventing" refer to a process by which a disease associated with SOD1 abnormalities is obstructed or delayed.

The terms "treatment", "treating" and the like are used herein to generally mean obtaining a desired pharmacological and/or physiological effect. The effect may be prophylactic in terms of completely or partially preventing a disease or symptom thereof and/or may be therapeutic in terms of a partial or complete cure for a disease and/or adverse effect attributable to the disease. It covers any treatment of a disease in an animal, and thus includes:

(a) preventing the disease from occurring in a subject which may he predisposed to the disease but has not yet been diagnosed as having it;

(b) inhibiting the disease, i.e., arresting its development; or (c) relieving the disease, i.e., causing regression of the disease.

By the term "treating" it is also intended, for the purposes of this invention, that the symptoms of the disease associated with SOD1 abnormalities be diminished or completely eliminated.

Those in need of treatment include those already with the disease as well as those prone to have the disease or those in which the disease is to be prevented.

According to yet another embodiment, the present invention provides for the use of at least one anti-abnormal SOD1 antibody for diagnosis of a disease associated with SOD1 abnormalities in an animal or for the preparation of a composition for diagnosis of a disease associated with SOD1 abnormalities in an animal. In a preferred embodiment, the antibody used for diagnosis is a monoclonal antibody and more preferably the monoclonal antibody is C4F6, D3H5 and/or B1G9.

3. Kits of the Invention

According to yet another embodiment, the present invention provides for a kit for diagnosis of a disease associated with SOD1 abnormalities in an animal.

Kits according of the invention may comprise packages, each containing one or more of the various components which are required to perform diagnostic tests. Components may be compounds, reagents, containers and/or equipment. Reagents are typically in concentrated form. For example, one container within a kit may contain a monoclonal antibody that specifically binds to an abnormal SOD1. The kits according to the invention are contemplated to be useful for detecting and/or quantifying abnormal SOD1 protein in biological (or other types of) samples. One or more additional containers may enclose elements, such as reagents or buffers, to be used in the assay. Such kits may also, or alternatively, contain a detection reagent as described above that contains a reporter group suitable for direct or indirect detection of antibody binding.

As may be appreciated, the anti-abnormal SOD1 antibody is preferably a monoclonal antibody and more preferably B1G9 and C4F6 or D3H5. The monoclonal antibody of the invention D3H5 may further be used in the kit of the invention as control.

In yet another embodiment, the present invention provides for a kit for treatment or prevention of a disease associated with SOD1 abnormalities in an animal.

The anti-abnormal SOD1 antibody contemplated is an antibody which specifically binds to an abnormal superoxide dismutase 1 (SOD1) and that neutralizes the pathologic effect of the abnormal SOD1 when administered to an animal such as a human. In a preferred embodiment of the invention, the antibodies of the treatment or prevention kit are monoclonal antibodies. Even more preferably, the antibodies are B1G9, S4F6 and D3H5.

4. The Method of Treatment

In a further embodiment, the invention provides for a method for preventing and/or treating a disease associated with SOD1 abnormalities in an animal such as a human. The method comprises the step of administering an effective amount of a composition.

The composition of the invention may be given to an animal through various routes of administration. For instance, the composition may be administered in the form of sterile injectable preparations, such as sterile injectable aqueous or oleaginous suspensions. These suspensions may be formulated according to techniques known in the art using suitable dispersing or wetting agents and suspending agents. The sterile injectable preparations may also be sterile injectable solutions or suspensions in non-toxic parenterally-acceptable diluents or solvents. They can be administered for example, by parenteral, intravenous, subcutaneous, intramuscular, intracranial, intraorbital, ophthalmic, intraventricular, intracapsular, intraspinal, intracisternal, intraperitoneal, ihtranasal, aerosol, by infusion or per os. Suitable dosages will vary, depending upon factors such as the amount of each of the components in the composition, the desired effect (short or long term), the route of administration, the age and the weight of the animal to be treated. Any other methods well known in the art may be used for administering the composition of the invention The present invention will be more readily understood by referring to the following examples. These examples are illustrative of the wide range of applicability of the present invention and are not intended to limit its scope. Modifications and variations can be made therein without departing from the spirit and scope of the invention. Although any methods and materials similar or equivalent to those described herein can be used in the practice for testing of the present invention, preferred methods and materials are described hereinafter

EXAMPLE 1

Generation of Monoclonal Antibodies According to Preferred Embodiments of the Invention Against Mutant SOD1

Mice monoclonal antibody against G93A SOD1 was generated. To produce monoclonal antibodies against human SOD1 mutant, BALB/c mice were immunized with rec G93A protein. Spleenocytes were then derived to generate hybridoma. Out of six clones generated, two clones showed specific immunoreactivity against G93A SOD1 by ELISA analysis. One clone called C4F6 exhibited selective reactivity for mutant SOD1 species including G93A, G37R and G85R with poor reactivity to WT SOD1.

EXAMPLE 2

Passive Immunization by Intraventricular Infusion of Anti-hSOD1 Antibody

Eight female C57Bl/6 mice at 3 months of age were immunized with recombinant human G93A SOD1 protein and antisera was affinity-purified and dialyzed against saline. The antibody was infused into ventricles through brain infusion cannula connected with osmotic minipump (model 2004, Alzet). The infusion rate of the pump was of 0.25 µl/hr to allow continuous treatment of the mice for 28 days (1.8 µg/day). The effect of passive immunization was evaluated by body weight, reflex score from hindlimb reflex and lifespan. To obtain the mouse antisera against mutant SOD1, eight female C57Bl/6 mice at 3 months of age were immunized with recombinant human G93A SOD1 protein and antisera was affinity-purified and dyalized against saline. Two weeks after the third immunization, the total blood was taken and the serum was obtained by centrifugation for 10 min at 12,000 g, room temperature. The serum was affinity-purified using an affinity column previously coupled with the recombinant G93A SOD1 protein (amino-link kit, Pierce, Rockford, Ill.). The antibody was dialyzed against saline with the concentration of 0.3 mg/ml and stored at −80° C. until use. The titration and specificity of the antisera was estimated by Western blotting. For control, the inventors infused saline or mouse IgG harvested from non-treated C57Bl/6 mice. The osmotic minipump (model 2004, Alzet) was filled with 200 µl of purified antibody or control saline, and connected to the brain infusion cannula (30 gauge, 3.0 mm height, Alzet, Palo Alto, Calif.) with polyvinylchloride catheter tube of 2.5 cm length. Transgenic mice G93A SOD1 at 85 days old were anesthetized with Xylazine-Kétamine (10 mg/ml). The sterile brain infusion cannula was implanted into the right ventricle stereotaxically. After insertion, the infusion cannula was fixed with dental cement. The osmotic minipump was implanted under the skin. The infusion rate of the pump was of 0.25 µl/hr to allow continuous treatment of the mice for 28 days (1.8 µg/day). To verify that intraventicularly infused antibodies penetrated into lumbar spinal cord, commercially available rabbit polyclonal anti-human SOD1 antibody (StressGen) or rabbit control IgG (DAKO) were conjugated with fluorescein isothiocyanate (FITC) (Pierce) before infusion with osmotic mini-pump. Sixteen days after installment of the pump, mice were sacrificed for immunofluorescent analysis and for Western blotting to test the activity of the residual antibody in the pump.

Measurement of body weight and hindlimb reflex was used to score the clinical effects because the Rotarod test presented a risk of fall-down resulting in pump damage. The extensibility and postural reflex of the hindlimbs when mice were pulled up with their tails were scored. Score 3 indicates full extension with normal postural reflex. Score 2 indicates moderate extension with normal postural reflex. Score 1 indicates poor extension and postural reflex whereas score 0 indicates

EXAMPLE 3

Therapeutic Effects of Immunization with Mutant Superoxide Dismutase in Mice Models of ALS There is emerging evidence for the existence of conventional secretory pathways for superoxide dismutase (SOD1) mutants linked to ALS and for neurotoxicity of extracellular mutant SOD1. This led the inventors to test immunization protocols aiming to reduce the burden of extracellular SOD1 mutant in nervous tissue of mice models of ALS, using bacterially-purified recombinant SOD1 mutant protein as an immunogen. Vaccination of hSOD1$^{G37R}$ mice by repeated injections of adjuvant-SOD1 mutant with a last boost injection before symptoms at 6 month-old was effective in delaying disease onset and extending life span by over 4 weeks. Microscopy examination of spinal cord samples revealed higher survival of motor neurons at end-stage of disease and more robust microglial activation in immunized hSOD1$^{G37R}$ mice as compared to those Injected with saline-adjuvant. Moreover, passive immunization through intraventricular infusion of purified anti-hSOD1 antibody with osmotic minipump alleviated disease symptoms and prolonged the lifespan of hSOD1$^{G93A}$ mice. Immunization is a potential therapeutic approach for familial ALS cases caused by SOD1 mutations.

Methods

Transgenic Mice

Transgenic mice carrying G37R mutant SOD1 (line 29), that overexpress by 5 folds human SOD1 protein as compared to endogenous mouse SOD1, were a generous gift from Dr. D. Cleveland (University of California, San Diego). Transgenic mice carrying mutant G93A SOD1 mutant (B6SJL-TgN [SOD1-G93A]dl 1 Gur) were purchased from Jackson laboratory. Mice were maintained heterozygous in the C57BV6 background mice.

Immunization Protocol and Mouse Analysis

Human G93A SOD1 recombinant protein was generated and purified from bacteria as previously described (Urushotani, et al., 2004 J. Neurochem, 90, 231-244). The study was conducted using littermates of G37R(N=8 and 7 for vaccinated and control mice, respectively) or G93A SOD1 (N=12 and 8 for vaccinated and control, respectively) mice. For the treatment of G37R SOD1 mice, eight G37R SOD1 transgenic mice (female=5, male=3) were vaccinated with recombinant G93A SOD1 whereas seven G37R SOD1 mice (female=4, male=3) were injected with saline-adjuvant. Four non-transgenic littermates were also treated with recombinant G93A SOD1 protein to estimate adverse reaction and serum titration. Immunization started at 2 months of age followed by two injections at three-week intervals with a last boost at 6 months old. Twelve G93A SOD1 mice were vaccinated with rec G93A while eight G93A SOD1 mice were injected with saline-adjuvant. Immunization was performed using Ribi adjuvant (Sigma). One vial was reconstituted by 2 ml of sterile saline with or without 500 µg of recombinant G93A SOD1 protein. After emulsification by intensive vortex, 200 µl of adjuvant-antigen solution (50 µg protein for two sites) was injected subcutaneously. The endpoint was defined as the time when mice become unable to turn back within 30 seconds after being put in lateral position. The survival data was analyzed by Kaplan-Meyer life span test and log-rank test. The statistical significance of the mean onset or survival was analyzed by student's t-test.

ELISA Assay

Antibody titer against human SOD1 of antisera or spinal cord tissues was measured by ELISA. 96-well plates were coated with 1 µg/ml of recombinant SOD1 protein (WT, G85R or G93A). After blocking in 5% BSA in PBS for 2 hr at room temperature, serially diluted mouse serum in TBS containing 1% BSA was added to each well and the plates incubated for 1 hr at room temperature. Detection was done with peroxidase-conjugated anti-mouse IgG and 2'-Azino-bis(3-ethylbenzthiazoline-6-sulfonic acid) Diammonium Salt (ABTS) as substrate. Absorption was read at a wavelength of 405 nm by ELISA reader (Molecular Devices, Sunnyvale, Calif.). Antibody titer was determined by the dilution at half level of maximum optical density.

Western Blotting

Total spinal cord lysates were prepared for Western blotting to titrate antisera of vaccinated mice, or to investigate the amount of G37R SOD1 after vaccination. Total tissue lysates from G37R SOD1 transgenic mice and from non-transgenic littermates were prepared by homogenization in 5× volume of TNG-T buffer consisting of 50 mM Tris-HCl pH 7.4, 150 mM NaCl, 10% glycerol, 1% Triton X100 and protease inhibitor cocktail (Roche). After 20 strokes in Teflon homogenizer, the tissue suspension was centrifuged for 10 min at 1000×g at 4° C., the supernatant was denatured in the sampling buffer containing 2-mercaptoethanol and SDS with boiling.

For the titration of antisera from vaccinated mice, 25 mg of lysates was used for Western blotting, using antisera at 1000 times dilution from vaccinated mice or saline-injected control mice. For controls, the membranes were reblotted with commercially available anti-human SOD1 (SOD-100, StressGen) and anti-actin antibodies (Chemicon). To analyze the amount of G37R SOD1 protein in the spinal cord from vaccinated mice, two different amounts of protein (5 and 10 µg/lane) from each mouse was analyzed by Western blotting, using SOD100 antibody, anti-actin antibody or monoclonal mouse anti-SOD1 antibody the inventors generated (see Example 1). The blot was detected using IgG conjugated with peroxidase and chemiluminescent assay. The Western bands were scanned and analyzed by densitometry using the software Scion Image (Scion Corp. Frederick, Md.).

Histochemical Analysis

Mice were perfused with 4% paraformaldehyde (PFA), post-fixed and incubated in anti-freezing agent. Immunohistochemistry was performed following standard protocols. The spinal cord sections of 25 µm were incubated with the primary antibody (1:800 for anti-Mac2 antibody) at 4° C. overnight. In the immunofluorescent experiment, sections were incubated with secondary antibody conjugated with fluorescent dye (Alexa 488, Molecular Probe) for 1 hr at room temperature. To detect endogenous immunoglobulin G in the spinal cord tissues, anti-mouse IgG conjugated with Alexa 594 was included together with another secondary antibody conjugated with Alexa 488. The sections were observed with confocal laser microscope (Olympus, Tokyo) under the same condition of the software settings (Fluoview, Olympus), including PMT, Gain, offset, C.A. and HeNe-G. Primary antibodies were visualized by the avidin-biotinimmunoperoxidase complex (ABC) method using Vectastain ABC kit (Vector Laboratories, Burlingame, Calif., USA) and 3,3'-diaminobenzidine tetrahydrochloride (DAB; Sigma). The number of motor neurons in the spinal cord sections was counted and averaged from the five slices of each mouse (n=4 for each group) stained with Toluidine blue (Nissl staining).

Results

Immunization Delays Disease Onset and Mortality in G37R SOD1 Mice

The inventors tested a vaccination approach in a mouse model reported to overexpress mutant SOD1$^{G37R}$ (line 42) at moderate levels (~4 folds the endogenous SOD1 levels) (24). As antigen for immunization, the inventors used recombinant metal-free human SOD1 mutant (apo-G93A) purified from in E. coli because of its misfolded nature and also because of its availability in the Applicant's laboratory. Immunization of SOD1$^{G37R}$ mice with either 50 μg of recombinant SOD1 mutant protein or saline in adjuvant was initiated at two months of age, followed by two subcutaneous injections at three-week intervals. The last injection of antigen- or saline-adjuvant was performed at 6 months of age (FIG. 1a).

The motor performance of SOD1$^{G37R}$ mice was assessed by the Rotarod test. As shown in FIG. 1B, there was rapid decline of motor performance at 50 weeks for ALS mice injected with saline-adjuvant whereas motor dysfunction was postponed by ~3 weeks in ALS mice vaccinated with SOD1 mutant (FIG. 1b). The disease onset, as defined by loss of 30% of motor performance, occurred at mean age of 53.1±0.2 weeks in vaccinated ALS mice as compared to 50.2±0.4 weeks in ALS mice injected with saline-adjuvant (FIG. 1c, p=0.0011). The effect of hSOD1 immunization on lifespan of ALS mice was also remarkable with a mean at 60.4±0.4 weeks as compared to 56.1±0.74 weeks for control mice injected with saline-adjuvant (FIG. 1d, p<0.0001). Thus, the immunization approach extended the longevity of ALS mice by 4.3 weeks.

Figure 1:
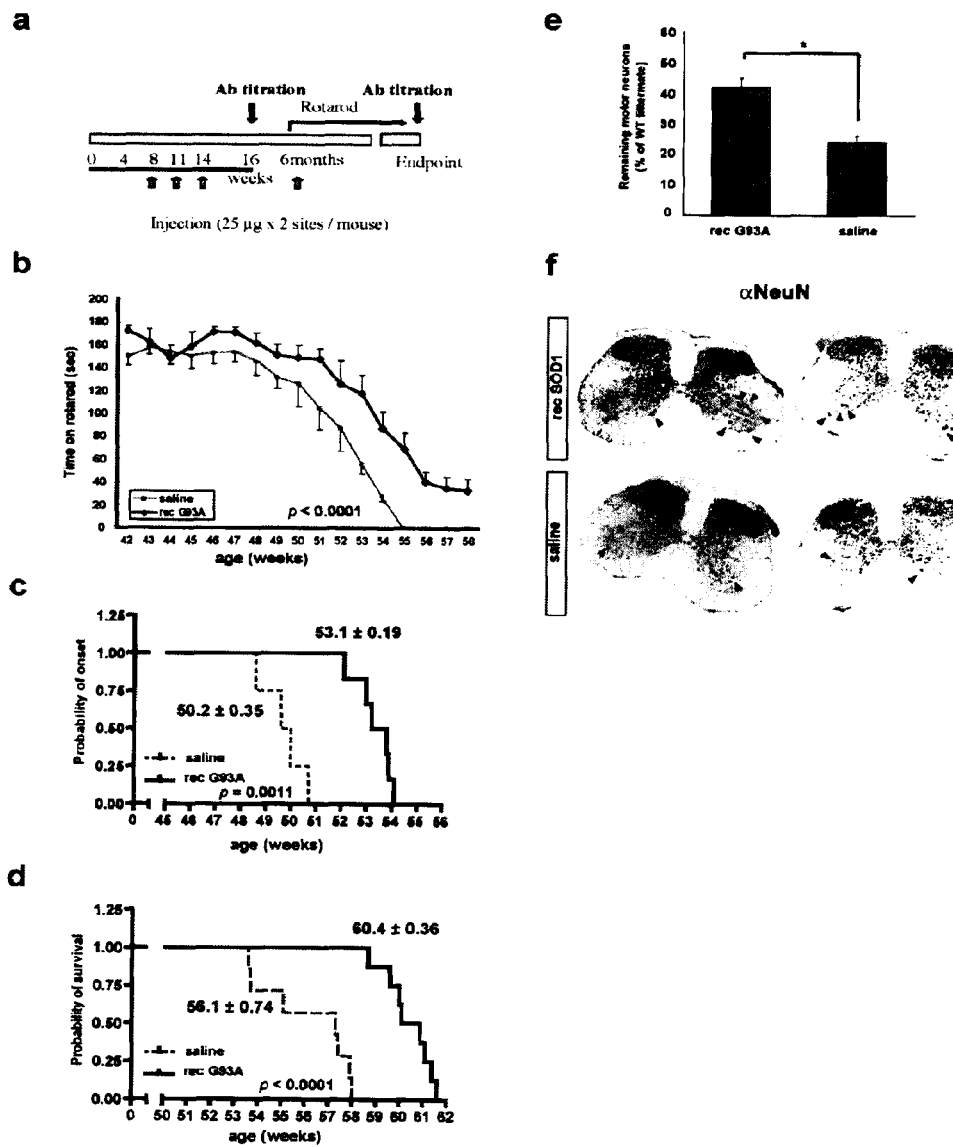
FIG. 1 (a-f) shows delayed onset and extension of lifespan in vaccinated G37R SOD1 mice a. The schedule of immunization. a: Early immunization. The mice were injected four times, starting at 2 months of age. Blood was collected for titration assay at 4 months of age and at end stage.

Attenuation of Motor Neuron Lose and Enhanced Microgliosis in Immunized ALS Mice To investigate whether immunization with mutant SOD1 resulted in neuroprotection, the inventors determined the number of Nissl-stained motor neurons in spinal cord sections of G37R SOD1 mice at end stage of disease (FIG. 1e). The number of remaining spinal motor neurons in ALS mice treated with saline-adjuvant corresponded to 24.1±2.0 percent the number of motor neurons in non-transgenic littermates. By comparison, end-stage ALS mice vaccinated with mutant SOD1 showed more surviving motor neurons with a number of remaining motor neurons corresponding to 41.9±3.1 percent. Immunohistochemistry with anti-NeuN antibody also revealed more surviving motor neurons at end stage in spinal cord of vaccinated ALS mice as compared to saline-adjuvant treated controls (FIG. 1f).

Figure 2:
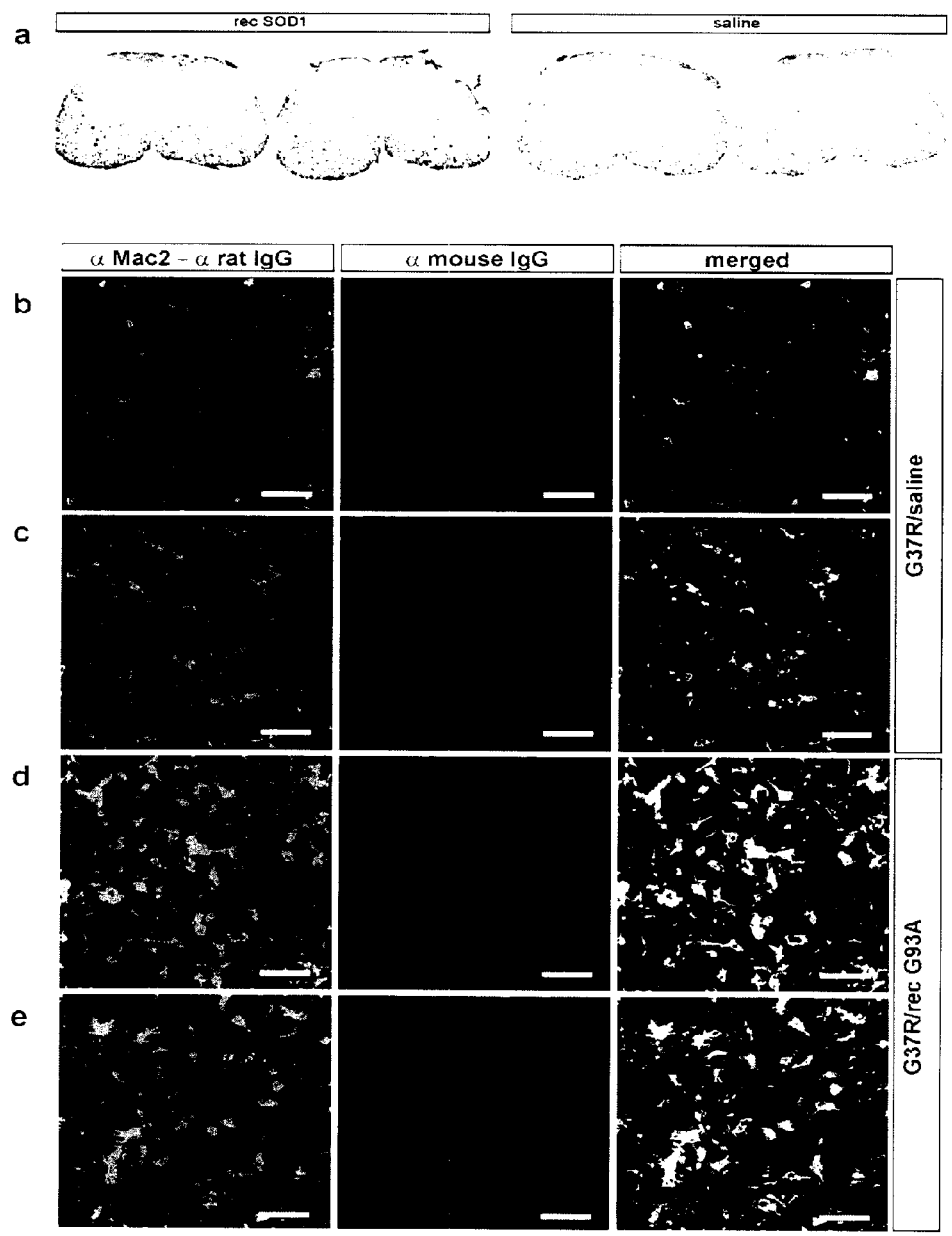

To investigate whether immunization was accompanied by an enhanced neuroinflammatory response, spinal cord sections were immunostained with rat monoclonal antibodies against Mac2, a marker of activated microglia. The microscopy studies showed enhanced microglial activation in ALS mice immunized with SOD1 mutant as compared to ALS mice injected with saline-adjuvant (FIG. 2a). The immunofluorescence signal for anti-Mac2 antibody followed by anti-rat IgG antibody conjugated with Alexa 488 was higher in spinal cord samples from vaccinated ALS mice than in mice injected with saline-adjuvant (FIG. 2b-e). The inventors also examined the immunofluorescence signals for endogenous immunoglobulin G (IgG) in spinal cord samples using anti-mouse IgG conjugated with red fluorescent (Alexa 594). The immunodetection signal for endogenous IgG was higher in samples from vaccinated mice. It should be noted that much of the IgG signal was colocalized with microglial cells (FIG. 2b-e, middle).

Correlation Between Antibody Titer and Longevity of G37R SOD1 Mice

The antibody titers in sera of ALS mice was determined at 4 months old and at the end stage of disease by ELISA using recombinant G93A SOD1 as antigen (Table 1). Despite the fact that the animals received the last antigen injection at 6 months of age in the early immunization group, the antibody titer against recombinant G93A SOD1 remained high in vaccinated mice until end stage of disease (FIG. 3a, Table 1). Lower antibody titers against G93A mutant SOD1 was noted in non-transgenic littermate mice injected with rec G93A (FIG. 3a, Table 1). Moreover, the scatter diagram in FIG. 3b revealed a direct correlation between the antibody titer in sera at 4 months old and the lifespan of ALS mice (significantly analyzed by Spearman's rho, P=0.0011). This would be consistent with a therapeutic effect of antibodies against SOD1 mutant.

Immunoblot analysis was carried out to demonstrate that the antisera from mice immunized with recombinant G93A SOD1 protein mutant were able to recognize the G37R SOD1 mutant protein. Unlike mice injected with saline-adjuvant, mice subjected to immunization produced antisera that yielded strong signals on immunoblots for the G37R SOD1 protein from spinal cord samples of ALS mice (FIG. 3c). Moreover, the inventors noted that antisera from rec G93A-vaccinated ALS mice produced higher reactivity to G85R SOD1 than to WT SOD1 (FIG. 3d, Table 2). Conversely, antisera from G37R SOD1 mice vaccinated with recombinant WT SOD1 protein (rec WT) exhibited low titers against mutant forms of SOD1 (FIG. 3d, Table 2). These data show that antibodies raised with mutant forms of SOD1 recognized preferentially the misfolded forms of SOD1.

Spinal Cord Lysates of Vaccinated Mice were Analyzed for the Presence of Anti-SOD1 Antibodies.

The G37R SOD1 mice immunized with rec G93A-adjuvant or with saline-adjuvant were sacrificed at 7 months old when antibody titers were the highest, and then spinal cord lysates were fractionated into cytosolic, heavy and light membrane fractions. The ELISA analysis demonstrated elevated titers of antibodies against rec-G93A SOD1 in both detergent-free buffer soluble and 1% TritonX100-soluble membrane fractions of spinal cord from mice vaccinated with rec G93A-adjuvant (FIG. 3e).

Evidence of Clearance of SOD1 Species in the Spinal Cord of Vaccinated Mice

To examine the effect of immunization in clearance of G37R SOD1 species, total spinal cord lysates were analyzed by Western blotting using either a rabbit polyclonal anti-human SOD antibody (SOD100) or a preferred monoclonal antibody of the invention (C4F6) with specificity for mutant SOD1 species generated by us. The C4F6 monoclonal was produced using standard procedures described above following immunization of mice with rec G93A protein (see Example 1). Interestingly, this monoclonal antibody recognizes the G93A SOD1 and to a lower extent other mutant SOD1 forms including G37R and G85R (FIG. 4a, b). However, the C4F6 exhibits very poor reactivity to the WT SOD1 (FIG. 4a). Western blot analysis spinal cord lysates using the C4F6 monoclonal revealed lower amount of mutant SOD1 species in vaccinated mice as compared to adjuvant-saline control mice (FIG. 4c,d). In contrast, with the use of the polyclonal anti-human SOD1 antibody (SOD100), there was no difference in SOD1 levels between vaccinated and control group (FIG. 1c). These results suggest that immunization ameliorated the disease of G37R mice by reducing the burden of subset of mutant SOD1, presumably misfolded species detectable with the C4F6 monoclonal.

Limited Effects of Vaccination in ALS Mice Expressing Extreme Levels of Mutant SOD1

The results above demonstrated beneficial effect of active immunization using a late onset model of ALS, the G37R SOD1 mouse line that moderately overexpresses mutant SOD1 by approximately 5 folds. The effect of vaccination with the widely used G93A SOD1 mice (B6SJL-TgN[SOD1-G93A]1Gur) that overexpress the mutant SOD1 mRNA by 40 folds and protein by 17 folds was further tested. As a result, these mice develop ALS symptoms quickly at 90 days old progressing to death at 130 days.

The active immunization was performed with the same protocol described above using recombinant G93A SOD1 as antigen. However, this vaccination approach did not succeed in altering significantly the clinical onset of disease and life span of the G93A SOD1 mice (FIG. 5a, b). A reasonable explanation for the failure of the vaccination approach with this ALS mouse model is that the amount of anti-SOD1 antibodies that passed the blood-brain-barrier was insufficient to neutralize such extreme levels of mutant SOD1 proteins in the nervous tissue.

As alternative approach, a passive immunization strategy was tested in G93A SOD1 mice based on direct intraventricular infusion of antibodies using an osmotic minipump (Alzet pump, Durect). The antisera for the passive immunization approach was obtained from C57B/6 mice vaccinated with recombinant human SOD1 mutant as described above. After affinity-purification and dialysis against saline (FIG. 5c), the antibody solution or control saline was infused into intraventricular space of presymptomatic G93A SOD1 mice (85 days old, N=5 for anti-SOD1 antibody, N=5 for control) using an osmotic mini-pump with 28 days duration (Alzet pump, Durect, Cupertino, Calif.). Disease progression was monitored by temporal profile of the body weight and hindlimb reflex score (see Methods). To verify the approach and penetrance of antibodies into lumbar spinal cord, the inventors first carried out the intraventricular infusion of FITC-conjugated rabbit polyclonal anti-human SOD1 antibody. Sixteen days after installment of the pump, the mice were sacrificed for examination of the spinal cord by immunohistochemistry. Immunofluorescent study revealed that FITC-labeled anti-human SOD1 antibody was frequently detected in spinal neurons with vesicular distribution (FIG. 6a, arrowheads) and occasionally in the active microglia (FIG. 6a arrows). This was less apparent in control IgG-FITC infusion (FIG. 6a, right). The residual antibody in the mini pump was collected and analyzed by Western blotting. The results show that the antibody remained active even after 16 days of subcutaneous implantation of the minipump (FIG. 6b). The passive immunization approach significantly delayed both body weight loss and hindlimb reflex impairment (FIG. 5d, e. P<0.05, two-way ANOVA). Moreover, the median survival of the immunized mice was 143 days whereas that of control mice is 135 (P=0.0256, Kaplan-Meyer life span test and log-rank test). The average lifespan of vaccinated mice was 141±1.4 whereas that of control mice was 135±1.5 (mean±standard error of mean, P<0.05 by student's-t test), resulting in significant prolongation of the lifespan by 1 week.

EXAMPLE 4

Reactivity of Anti SOD1 Monoclonal Antibodies According to Preferred Embodiments of the Invention ELISA Assay for 6 Monoclonal Antibodies Against SOD1

Well plates were coated with 1 µg/ml of recombinant SOD1 protein (WT or G93A). After blocking in 5% BSA in PBS for 2 hr at room temperature, serially diluted mouse serum in TBS containing 1% BSA (½, ⅒, 1/20 and 1/40) was added to each well and the plates incubated for 1 hr at room temperature. Detection was done with peroxidase-conjugated anti-mouse IgG and 2'-Azino-bis(3-ethylbenzthiazoline-6-sulfonic acid) Diammonium Salt (ABTS) as substrate. Absorption was read at 450 nm.

As it is clear from FIG. 6 and Table 3, the monoclonal antibodies clones B1G9 and C4F6 exhibited specific reactivity for the mutant SOD1 whereas other clones showed reactivity for either normal or mutant SOD1 forms. The clone D3H5 has high affinity for normal and mutant SOD1 species.

EXAMPLE 5

Specific Immunohistochemistry Detection of Mutant SOD1 Species in Mouse Spinal Cord Samples by a Preferred Monoclonal Antibody of the Invention (C4F6)

Normal mice or transgenic mice expressing human WT SOD1 (J2429) or mutant SOD1 (G93A or G37R) were perfused with 4% paraformaldehyde (PFA), post-fixed and incubated in anti-freezing agent. The spinal cord sections of 25 µm obtained from presymptomatic mutant SOD1 transgenic mice (G37R and G93A) or human WT transgenic mice were stained using mouse monoclonal anti-human SOD1 antibody (C4F6 clone). For that the spinal cord sections were incubated with the primary antibody (1:500 for C4F6 antibody) at 4° C. overnight followed by biotinylated anti-IgG antibody. Primary antibodies were visualized by the avidin-biotinimmunoperoxidase complex (ABC) method using Vectastain ABC kit (Vector Laboratories. Burlingame, Calif., USA) and 3,3'-diaminobenzidine tetrahydrochloride (DAB; Sigma).

Immunostaining was detected in samples for transgenic mice expressing mutant SOD1 species (G93A and G37R) but not from mice expressing human WT SOD1 (J2429) (FIG. 15).

EXAMPLE 6

Specificity of a Preferred Monoclonal Antibody of the Invention (C4F6) to the Mutant SOD1 Forms With reference to FIG. 16 the inventors have shown that vaccination with SOD1 mutant can confer protection by reducing the CNS amount of mutant SOD1 species reactive to C4F6 antibodies.

FIG. 16a shows the Western blot analysis showing that the C4F6 mouse monoclonal antibody recognizes the mutant SOD1 forms (G37R and G93A) but not the WT SOD1 from spinal cord extracts of transgenic mice. FIG. 16b shows the ELISA analysis showing that the C4F6 monoclonal detects the G85R metallated SOD1 protein but not the WT metallated SOD1 recombinant protein. And finally FIG. 16c shows the Western blotting analysis of spinal cord extracts showing lower amount of mutant SOD1 species detected by C4F6 antibody in vaccinated mice as compared to adjuvant-saline control mice. Five and ten micrograms of protein from each mouse were loaded onto each well for Western analysis. Three mice from both vaccinated and saline-injected mice were analyzed.

EXAMPLE 7

Screening of Mutant SOD1 by Western Blots of Blood Samples Using a Preferred Monoclonal Antibody of the Invention (C4F6)

Blood samples (100 μL) taken from transgenic mice expressing mutant SOD1 G93A, expressing human WT SOD1 or taken from normal mice were centrifuged 15 min at 1000×g at 4° C. The pellet was incubated in 10 mM Tris-HCl (pH 7.4) for 1 h on ice. Samples were centrifuged for 20 min at 20,000×g at 4° C. and the supernatant collected and boiled in SDS-sampling buffer for 5 min. The samples were fractionated on SDS-PAGE and blotted according to standard procedures. For detection of bands, the blots were treated with IgG conjugated with peroxidase and chemiluminescent assay.

With reference to FIG. 17, the upper panel shows the immunoblots of blood samples using the C4F6 monoclonal from normal mice (1-5), from mice expressing mutant SOD1 G93A (lanes 6-10) and from mice expressing human WT SOD1 (lanes 11-14). The lower panel shows the immunoblots of blood samples using rabbit polyclonal anti-human SOD1 (StressGen, Victoria. BC) from normal mice (1-5), from mice expressing mutant SOD1 G93A (lanes 6-10) and from mice expressing human WT SOD1 (lanes 11-14).

FIG. 17 shows that the monoclonal antibody C4F6 detects the mutant SOD1 (G93A) but not the normal WT SOD1 species in blood samples from transgenic mice expressing human SOD1 genes. The results demonstrate that this antibody can be used for diagnostic screen of mutant SOD1 species through simple blood test.

EXAMPLE 8

Immunohistochemistry Detection of WT or Mutant SOD1 Species in Mouse Spinal Cord Samples by a Preferred Monoclonal Antibody of the Invention (D3H5)

Normal mice or transgenic mice expressing human WT SOD1 (J2429) or mutant SOD1 (G93A or G37R) were perfused with 4% paraformaldehyde (PFA), post-fixed and incubated in anti-freezing agent. The spinal cord sections of 25 μm obtained from presymptomatic mutant SOD1 transgenic mice (G37R and G93A) or human WT transgenic mice were stained using a preferred monoclonal anti-human SOD1 antibody of the invention (D3H5). For that the spinal cord sections were incubated with the primary antibody (1:500 for D3H5 antibody) at 4° C. overnight followed by biotinylated anti-IgG antibody. Primary antibodies were visualized by the avidin-biotinimmunoperoxidase complex (ABC) method using Vectastain ABC kit (Vector Laboratories, Burlingame, Calif., USA) and 3,3'-diaminobenzidine tetrahydrochloride (DAB; Sigma) (FIG. 18).

EXAMPLE 9

Wild Type SOD1 Acquires Binding and Toxic Properties of ALS-Linked Mutant Forms Through Oxidation Materials and Methods
Plasmids and Antibodies Mammalian expression plasmid carrying human SOD1 tagged with FLAG (pcDNA3-FLAG-SOD1) or mouse chromogranin B tagged with HA (pcDNA3-CgB-HA) were generated as previously described by Urushitani et al., 2006, Nature Neurosc, 9, 108-118. Rabbit monoclonal anti-human SOD1 (SOD-100) and mouse monoclonal Hsp/Hsc70 antibodies were purchased from StressGen (Victoria, BC). Rat monoclonal anti-HA (3F10), mouse monoclonal non-phosphorylated neurofilament H (SMI32), mouse monoclonal anti-actin (C4) antibodies were purchased from Roche (Basel, Switzerland), Steinberger Monoclonal Inc. (Baltimore, Mass.) and Chemicon (Temecula, Calif.). Anti-chromogranin B (26102) and COX-IV (A-6431) antibodies were purchased from QED Bioscience (San Diego, Calif.) and Molecular Probes (Eugene, Oreg.). Mouse monoclonal Anti syntaxin-1 (HPC1) and Akt1 (B-1) were from Santa Cruz (Santa Cruz, Calif.). Rabbit polyclonal antibody against mouse/rat TGN-38 was generated as previously described by Urushitani et al., 2006, Nature Neurosc, 9, 108-118.

Cultures, Transfection and Drug Treatment

Murine neuroblastoma cell line, Neuro2a cells were maintained in Dulbecco's modified essential medium (DMEM) containing 10% fetal bovine serum (FBS). Transfections were performed using Lipofectamin PLUS (Invitrogen, Carlsbad, Calif.) according to the manufacturer's protocol. At 3 hrs after transfection, the medium was replaced with the nutrient medium containing 2 mM dibutyryl cyclic-AMP (db-cAMP). At 24 hrs after transfection, cells were exposed to 1.5 mM hydrogen peroxide ($H_2O_2$) or sterile water (control) for 45 min for further analysis. Murine microglial cell line BV2 cells were maintained in DMEM/F12 Ham's medium (DF) containing 10% FBS. Except from the initial plating, antibiotics were not included in culture medium.

Immunoblotting and Immunoprecipitation

Cultured cells were washed twice in PBS and harvested in TNG-T buffer consisting of 50 mM Tris-HCl pH 7.4, 150 mM NaCl, 10% glycerol, 1% Triton X-100 and a protease inhibitor cocktail (Roche, Mannheim, Germany). After 1 hr-incubation on ice, cell suspension was centrifuged (15000 rpm for 20 min), and the supernatant was collected. To investigate the effect of the treatment of the cell with $H_2O_2$, the lysates were incubated with anti-FLAG affinity gel (M2, Sigma, St. Louis, Mo.) for 1 hr at 4° C. The immunoprecipitates were eluted in 4% SDS sampling buffer, and separated by SDS-polyacrylamide gel electrophoresis (denaturing-PAGE) and transferred to polyvinylidene difluoride (PVDF) membrane (PerkinElmer, Boston, Mass.) for Western analysis. A Western blot image was obtained using a Western lightning chemiluminescence reagent (PerkinElmer).

In Vivo Ubiquitination

The modification of human SOD1 by poly-ubiquitin chain is investigated by in vivo ubiquitination experiment (see Urushitani et al., 2002, J. Neurochem 83, 1030-1042. Neur2a cells were cotransfected with FLAG-tagged hSOD1 (WT or G93A mutant) and HA-tagged ubiquitin. After exposure to $H_2O_2$, cells were harvested in TNG-T buffer containing protease inhibitor cocktail in the same protocol mentioned above. The lysates were immunoprecipitated using anti-FLAG affinity gel (M2, Sigma), and eluates from immunobeads were analyzed by Western blotting using anti-HA (Roche) and anti-human SOD1 (StressGen) antibodies.

Purification of Recombinant Proteins

Recombinant glutathione S-transferase fused hSOD1 (GST-hSOD1) was generated as reported by Urushitani et al., 2002, J. Neurochem 83, 1030-104. Metallation of hSOD1 was performed by overnight incubation with 20 mM of $ZnCl_2$ and three hours incubation with 20 mM of $CuCl_2$, followed by overnight dialysis against PBS. Moreover, the oxidization of the recombinant holo-hSOD1 was performed by one hour incubation at room temperature with 0.1 mM of $H_2O_2$ followed by subsequent dialysis against PBS overnight. The recombinant proteins were stored at −80° C. until use.

Subcellular Fractionation

Neuro2a cells were transiently transfected with FLAG-tagged SOD1 (WT and G93A) in six-well culture plates. 24 hrs after transfection, cells were treated with 1.5 mM of hydrogen peroxide in DMEM for 30 minutes, and subsequently incubated in the nutrient medium eliminating $H_2O_2$ for further 30 minutes. Harvested cells were homogenized in homogenization buffer (250 mM sucrose, 10 mM Tris-HCl (pH 7.4), 1 mM $MgCl_2$ and protease inhibitor cocktail), and centrifuged for 15 min at 1000 g to exclude debris. The supernatant was further centrifuged at 8000 g for 15 min to separate pellet (heavy membrane fraction) and the supernatant. The supernatant was ultracentrifuged at 105,000 g for 60 minutes to obtain the cytosolic fraction (supernatant) and the light membrane fraction (pellet). Each pellet was resuspended in the homogenization buffer containing 1% Triton-X100 with brief sonication. Equal amounts of protein were analyzed by Western blotting after determination of the protein concentration with Bradford assay (BioRad, Hercules, Calif.).

Semi-Quantitative RT-PCR

Murine microglial cell-line, BV2 cells at 90% confluency in six-well culture plates, were treated with PBS, LPS (10 μg/ml), WT SOD1 (10 μg/ml), oxidized WT SOD1 (10 μg/ml) or with G93A SOD1 (10 μg/ml) for 24 hours. All SOD1 recombinant proteins were previously metallated. Total RNA was extracted from total cell lysates using Trizol reagent (Invitrogen) according to manufacturer's instructions. First strand cDNA was synthesized from total RNA using reverse transcriptase and oligo-dT primer (Invitrogen). The expression level of Tumor Necrosis Factor (TNF-α), inducible nitric oxide synthase (iNOS) and GAPDH was estimated by PCR. The primer pairs used in this experiment are 5' TCAGTGAGACCACTGCAATG 3' (SEQ ID NO 1) and 5' GTGGAGTGAGACTTTGGATG 3' (SEQ ID NO 2) for TNF-α; 5' CCTTGTGTCAGCCCTCAGA 3' (SEQ ID NO 3) and 5' CACTCTCTTGCGGACCATCTC 3' (SEQ ID NO 4) for iNOS and finally 5' GGCATTGTG-GAAGGGCTCA 3' (SEQ ID NO 5) and 5' TCCACCACCCT-GTTGCTGT 3' (SEQ ID NO 6) for GAPDH.

Primary Culture of Mouse Embryonic Spinal Cord

Primary dissociated cultures from embryonic mouse spinal cord were prepared as described by Urushitani et al., 2002, J. Neurochem 83, 1030-104. Twelve days after plating, cultures were treated with recombinant proteins (human WT SOD1, human oxidized WT SOD1 and human G93A SOD1 for 24 hrs, followed by fixation in 4% paraformaldehyde (PFA). The motor neuron viability was estimated by immunocytochemistry using anti-non-phosphorylated neurofilament H (SMI32; 1:500). Motor neurons were identified as SMI32-immunoreactive large neurons (>20 μm) with a single long extending axon. Anti-mouse IgG conjugated with Alexa 488 was used as secondary antibody. Cultures were observed under fluorescent microscope and four images from randomly selected fields were obtained from 3 sister cultures. The number of motor neurons was obtained from each field and cell density (cells/cm2) was calculated.

Results

Misfolding of WT SOD1 by Oxidative Stress

To test the hypothesis that SOD1 may be a target protein of oxidative stress in neurodegeneration, the inventors treated bacterially purified recombinant SOD1 proteins (WT G85R and G93A) with 1 mM hydrogen peroxide ($H_2O_2$) for 30 min at 37° C., and analyzed its migration pattern and solubility. Western analysis of total fractions of $H_2O_2$-treated recombinant SOD1 showed remarkable change in migration pattern, fragmentation and high molecular aggregate formation (FIG. 10A, lanes 2, 4 and 6). Moreover, ultracentrifugation of the recombinant protein after $H_2O_2$ treatment revealed that such oxidation-related species were exclusively detected in pellet fraction, but not in supernatant (FIG. 10B). Only monomer and dimer SOD1 species were detected in supernatant. Although WT SOD1 is less susceptible to oxidative stress than mutant SOD1, the molecular change obtained from Western analysis is definitely similar to mutants. These in vitro results indicate that oxidation affects the misfolding and aggregation of WT SOD1 as well as mutant SOD1. The results according to the present invention are consistent with previous report showing that oxidation of WT SOD1 promotes its aggregation in vitro analyzed by light scattering assay. To further investigate the oxidation of WT SOD1 in vivo, Neuro2a cells were transfected with WT and G93A SOD1 tagged with FLAG peptides at N'-terminus and were exposed to 1.5 mM $H_2O_2$ for 45 min at 24 hrs after transfection. Then, pull-down assay of the transfected cell lysates using anti-FLAG affinity gel revealed that Hsp/Hsc700 was co-immunoprecipitated with mutant G93A, oxidized WT SOD1, but not with non-oxidized WT SOD1 (FIG. 11A). It is concluded that oxidation by $H_2O_2$ cause a misfolding of WT SOD1 with ensuing interaction with Hsp/Hsc70.

Oxidized WT SOD1 can be Conjugated to Poly-Ubiquitin

Most types of ALS-related SOD1 mutant proteins are degraded by the ubiquitin-proteasomal pathway. Based on this notion, the inventors performed in vivo ubiquitination experiment to investigate whether oxidation transforms WT SOD1 protein to misfolded species suitable for poly-ubiquitination. Neuro2a cells were transfected with FLAG-tagged WT or G93A SOD1s together with HA-tagged ubiquitin and then exposed to 1.5 mM $H_2O_2$ for 45 min before harvesting. Western blot analysis of total cell lysates and anti-FLAG immunoprecipitates shows that WT SOD1 in $H_2O_2$-treated cells was conjugated with multi-ubiquitin chain unlike WT SOD1 from untreated cells. The same phenomenon was observed with G93A mutant SOD1 (FIG. 11B).

Oxidized WT-SOD1 Interacts with Chromogranin B

The inventors have previously identified chromogranin B (CgB) as a binding partner of mutant SOD1. Chromogranins were found to interact and to promote secretion of mutant SOD1 species. To test whether oxidized WT SOD1 species can interact with chromogranins, Neuro2a cells were transfected with FLAG-tagged WT or G93A SOD1s together with mouse HA-tagged CgB. At 24 hrs post-transfection, cells were exposed to 1.5 mM $H_2O_2$ for 45 min before harvesting. Western blot analysis of fractionated Neuro2a cell lysates showed that both WT and mutant SOD1 distributed in the microsomal fraction where CgB is abundantly expressed (FIG. 12A). Treatment with hydrogen peroxide did not affect protein levels of WT and mutant SOD1 in subcellular fractions. Total cell lysates were immunoprecipitated with anti-FLAG affinity gel and analyzed by Western blotting. As shown in FIG. 12B, CgB was co-immunoprecipitated with either G93A SOD1 or oxidized WT SOD1, but not with intact WT SOD1. This result indicates that oxidation of WT SOD1, which distributes in ER-Golgi compartments, induces its binding to chromogranins.

Oxidized WT SOD1 can Induce Microglial Activation and Death of Motor Neurons

There is evidence that both WT and mutant SOD1 species are secreted. However, unlike WT SOD1, secreted mutant SOD1 induces proinflammatory molecules such as TNF-α, iNOS and COX2. To examine whether oxidized WT SOD1 can mimic mutant SOD1 in activating microglia, murine microglial BV2 cells were exposed to bacterially purified recombinant holo-SOD1 that was treated or not with $H_2O_2$. Semi-quantitative RT-PCR experiment revealed that exposure of BV2 cells to either G93A SOD1 or oxidized WT SOD1 induced the expression of TNF-α and iNOS (FIG. 13).

Unlike WT SOD1, extracellular mutant SOD1 can induce the death of cultured motor neurons even in absence of microglia. Here, embryonic spinal cord cultures were exposed to either recombinant WT SOD1, oxidized WT SOD1 or G93A SOD1 (0.5 and 1.0 µg/ml) for 24 hours. As expected, WT SOD1 was not toxic to motor neurons in this concentration range. However, oxidized WT SOD1 exhibited toxicity to cultured motor neurons in a dose-dependent manner like G93A mutant SOD1 (FIG. 14). The inventors also observed microglial activation in the mixed culture characterized by large ameboid cell morphology (data not shown). These results indicate that oxidized WT SOD1 acquires the neurotoxic property of mutant SOD1 species.

Discussion

From the results presented here, the inventors conclude that WT SOD1 acquires through oxidation many of the binding and toxic properties of ALS-linked mutant SOD1. This conclusion is supported by the following results: 1) $H_2O_2$-treated recombinant WT SOD1 yielded aggregates similar to those of mutant SOD1 species, 2) oxidation induces misfolding of WT SOD1 as revealed by the interaction with Hsp/Hsc70 and by the multi-ubiquitination, 3) oxidized WT SOD1 distributed in membrane fractions and interacted with neurosecretory protein CgB in the transfected neuronal cells and, 4) extracellular oxidized WT SOD1 triggered microglia activation and death of cultured motor neurons.

There are multiple lines of evidence for involvement of oxidative stress in the pathogenesis of neurodegenerative diseases including Parkinson's, Alzheimer's diseases and ALS. Considering the abundance of SOD1 comprising 1% of the total protein, and its role as antioxidant, it is plausible that SOD1 may be a target of oxidative stress in neurodegenerative diseases. Actually, the oxidation of WT SOD1 is a well established phenomenon. $H_2O_2$ can interact with the active site of WT SOD1 and may inactivate the enzyme through hydroxyl radical production. Rakhit et al., (2004, J. Biol. Chem., 279, 15499-15504) found that WT SOD1 possesses four oxidation-prone amino acids (His48, 80, 120 and Phe20) and that their oxidation triggers SOD1 aggregation. In addition, oxidation of cysteine residues in WT SOD1 can also provoke its misfolding and aggregation via intermolecular disulfide.

The results according to the present invention demonstrate that oxidized WT SOD1 interact with the neurosecretory protein CgB like the mutant SOD1 forms. Once secreted in the milieu, the extracellular oxidized WT SOD1 activates microglial cells and induce motor neuron death (FIG. 14). Such model of toxicity based on secreted oxidized WT or mutant SOD1 is compatible with the view that the disease is not strictly autonomous to motor neurons and that multiple cell types contribute to the disease including motor neurons, interneurons, microglia and astrocytes. It also explains how the damage can be propagated from one cell to another, as seen from the analysis of chimeric mice expressing mutant SOD1.

In the light of results presented here, a role for SOD1 in pathogenesis of other neurodegenerative diseases cannot be excluded either. A recent report by Choi et al., 2005, J. Biol. Chem, 280, 11848-11655 showed that SOD1 is oxidized in the brain lysates from patients with Alzheimer's and Parkinson's diseases and that oxidized SOD1 proteins are also present in senile plaques and Lewy bodies.

TABLE 1

Serum titration by ELISA for antibody against G93A SOD1 in immunized mice

| Composition | Age | Mice | Ab titer | N |
|---|---|---|---|---|
| rec G93A | 4 mo. | G37R | 2967.3 ± 1413.50 | 7 |
|  | End | G37R | 1183.5 ± 721.2 | 6 |
|  | 4 mo. | non-Tg | 648.1 ± 278.25 | 4 |
| saline | 4 mo. | G37R | 31.9 ± 1.23 | 6 |
|  | End | G37R | 63.6 ± 2.22 | 4 |

Antibody titration of sera from mice in vaccinated mice by enzyme-linked immunosorbent assay (ELISA).

TABLE 2

ELISA data showing different reactivity of antisera from mice immunized with WT or mutant SOD1 species.

| | immunized | | Target antigens in ELISA | | |
|---|---|---|---|---|---|
| Tg mice | by | N | WT | G85R | G93A |
| G37R | rec G93A | 3 | 411.4 ± 181.75 | 720.24 ± 228.85 | 1446.23 ± 324.64 |
| G37R | rec WT | 3 | 424.3 ± 4.48 | 227.74 ± 76.33 | 229.7 ± 52.07 |
| non Tg | rec G93A | 3 | 571.7 ± 319.60 | 672.17 ± 242.03 | 1123.9 ± 233.23 |

TABLE 3

Antibody titers for recombinant human WT, G85R or G93A SOD1 metallated protein were determined by ELISA.

| | | Dilution (1/x) | Dilution 1/2 | Dilution 1/10 | Dilution 1/20 | Dilution 1/40 |
|---|---|---|---|---|---|---|
| B1G9 | mutant | | 1.147 | 1.320 | 0.939 | 0.889 |
| | Non-mutant | | 0.014 | 0.009 | 0.011 | 0.010 |
| D3H5 | mutant | | 1.807 | 2.198 | 2.023 | 2.055 |
| | Non-mutant | | 1.765 | 2.004 | 2.034 | 1.787 |
| D4G6 | mutant | | 2.050 | 1.980 | 1.653 | 1.210 |
| | Non-mutant | | 1.773 | 1.768 | 1.364 | 1.163 |
| C10F10 | mutant | | 1.336 | 1.684 | 1.65 | 1.627 |
| | Non-mutant | | 1.178 | 1.307 | 1.357 | 1.497 |
| C4F6 | mutant | | 2.180 | 1.893 | 1.622 | 1.441 |
| | Non-mutant | | 0.885 | 0.222 | 0.110 | 0.075 |
| B9G12 | mutant | | 1.179 | 1.134 | 1.030 | 0.941 |
| | Non-mutant | | 0.759 | 0.654 | 0.601 | 0.520 |

The invention claimed is:

1. A hybridoma cell line deposited with the International Depositary Authority of Canada on Aug. 29, 2006 under accession number ADI-290806-03.

2. A monoclonal antibody produced by the hybridoma cell line according to claim 1 or an antigen-binding fragment thereof.

3. A method for treating amyotrophic lateral sclerosis associated with SOD1 abnormalities in an animal, said method comprising the step of administering an effective amount of at least an antibody as defined in claim 2.

4. The method of claim 3, wherein amyotrophic lateral sclerosis is familial amyotrophic lateral sclerosis.

5. The method of claim 3, wherein amyotrophic lateral sclerosis is sporadic amyotrophic lateral sclerosis.

6. A composition comprising a pharmaceutically acceptable carrier and at least an antibody as defined in claim 2.

7. A method for treating amyotrophic lateral sclerosis associated with SOD1 abnormalities in an animal, said method comprising the step of administering an effective amount of a composition as defined in claim 6.

8. The method of claim 7, wherein amyotrophic lateral sclerosis is familial amyotrophic lateral sclerosis.

9. The method of claim 7, wherein amyotrophic lateral sclerosis is sporadic amyotrophic lateral sclerosis.

10. A method for the diagnosis of amyotrophic lateral sclerosis associated with SOD1 abnormalities in a biological sample of an animal, the method comprising steps of:
    contacting at least an antibody as defined in claim 2 with the biological sample, and
    detecting the presence of a specific binding of the antibody with an abnormal SOD1 protein, the presence of the specific binding indicating the presence of amyotrophic lateral sclerosis in the animal.

11. A kit for treatment or prevention of a disease amyotrophic lateral sclerosis associated with SOD 1 abnormalities in an animal, said kit comprising at least a container, said container containing at least an antibody as defined in claim 2.

12. The kit of claim 11, wherein amyotrophic lateral sclerosis is familial amyotrophic lateral sclerosis.

13. The kit of claim 12, wherein amyotrophic lateral sclerosis is sporadic amyotrophic lateral sclerosis.

* * * * *